US009086412B2

(12) United States Patent
Taylor et al.

(10) Patent No.: US 9,086,412 B2
(45) Date of Patent: Jul. 21, 2015

(54) EXTRACELLULAR VESICLE-ASSOCIATED PROTEIN MARKERS OF CANCER

(71) Applicant: University of Louisville Research Foundation, Inc., Louisville, KY (US)

(72) Inventors: Douglas D. Taylor, Louisville, KY (US); Cicek Gercel-Taylor, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

(21) Appl. No.: 13/795,924

(22) Filed: Mar. 12, 2013

(65) Prior Publication Data

US 2014/0186264 A1 Jul. 3, 2014

Related U.S. Application Data

(60) Provisional application No. 61/747,612, filed on Dec. 31, 2012.

(51) Int. Cl.
*G01N 33/53* (2006.01)
*G01N 33/574* (2006.01)

(52) U.S. Cl.
CPC .... *G01N 33/57415* (2013.01); *G01N 33/57449* (2013.01); *G01N 33/57484* (2013.01)

(58) Field of Classification Search
CPC ...................................................... A61K 39/00
See application file for complete search history.

(56) References Cited

U.S. PATENT DOCUMENTS

| | | | |
|---|---|---|---|
| 6,329,209 | B1 | 12/2001 | Wagner |
| 6,365,418 | B1 | 4/2002 | Wagner |
| 6,406,921 | B1 | 6/2002 | Wagner |
| 6,475,808 | B1 | 11/2002 | Wagner |
| 6,475,809 | B1 | 11/2002 | Wagner |
| 8,216,784 | B2 | 7/2012 | Taylor et al. |
| 2012/0070848 | A1 | 3/2012 | Rak et al. |

FOREIGN PATENT DOCUMENTS

| | | |
|---|---|---|
| WO | 2010/141955 | 12/2010 |

OTHER PUBLICATIONS

Ramacciotti et al (Thromb Res, 2010, 125(6): Abstract).*

Tockman et al (Cancer Res., 1992, 52:2711s-2718s).*

Choi et al., "Quantitative proteomics of extracellular vesicles derived from human primary and metastatic colorectal cancer cells," Journal of Extracellular Vesicles, 1(Article 18704):1-15 (2012).

International Search Report and Written Opinion issued in PCT/US2013/077202 on Apr. 1, 2014 (10 pages).

Zhu et al., "Abnormal expression of fibrinogen gamma (FGG) and plasma level of fibrinogen in patients with hepatocellular carcinoma," Anticancer Research, 29(7):2531-2534 (2009).

Al-Nedawi et al., "Intercellular Transfer of the Oncogenic Receptor EGFRvIII by Microvesicles Derived from Tumour Cells," *Nature Cell Biol.* 10:619-624, 2008.

Atay, et al., "Human Trophoblast-Derived Exosomal Fibronectin Induces Pro-Inflammatory Il-1β Production by Macrophages," *Am. J. Reprod. Immunol.* 66:259-269, 2011.

Atay et al., "Trophoblast-Derived Exosomes Mediate Monocyte Recruitment and Differentiation," *Am. J. Reproduct. Immunol.* 65:65-77, 2011.

Tauro et al., "Comparison of Ultracentrifugation, Density Gradient Separation, and Immunoaffinity Capture Methods for Isolating Human Colon Cancer Cell Line LIM1863-Derived Exosomes," *Methods* 56:293-304, 2012.

Jemal et al., "Cancer Statistics, 2004," *CA Cancer J. Clin.* 54(1):8-29, 2004 (Abstract).

Shi et al., "Exploring the Uncertainties of Early Detection Results: Model-Based Interpretation of Mayo Lung Project," *BMC Cancer* 11:92, 2011.

Memarzadeh et al., "Advances in the Management of Epithelial Ovarian Cancer," *J. Reprod. Med.* 46:621-629, 2001.

Hoskins, "Prospective on Ovarian Cancer: Why Prevent?" *J. Cell. Biochem. Suppl.* 23:189-199, 1995 (Abstract).

Taylor et al., Serum/Plasma Proteomics, Chapter 15, "Extracellular Vesicle Isolation for Proteomic Analyses and RNA Profiling," Springer Science, 2011.

* cited by examiner

*Primary Examiner* — Sean Aeder
(74) *Attorney, Agent, or Firm* — Fish & Richardson P.C.

(57) ABSTRACT

Extracellular vesicle-associated protein biomarkers for use in diagnosing and staging carcinomas, e.g., lung and ovarian cancers.

18 Claims, 10 Drawing Sheets
(8 of 10 Drawing Sheet(s) Filed in Color)

EXTRACELLULAR VESICLE-ASSOCIATED PROTEIN MARKERS OF CANCER

CROSS-REFERENCE TO RELATED APPLICATIONS

This application claims priority to U.S. Provisional Patent Application Ser. No. 61/747,612, filed Dec. 31, 2012, the entire contents of which are incorporated by reference herein.

TECHNICAL FIELD

This invention relates to extracellular vesicle-associated protein biomarkers for use in diagnosing and staging carcinomas, e.g., lung and ovarian carcinomas, and distinguishing these from benign tumors.

BACKGROUND

Poor early detection coupled with ineffective treatments for advanced disease is responsible for the low 5-year survival rates of certain cancers, including ovarian and lung cancers. Development of new diagnostic/prognostic markers would significantly enhance disease detection and improve survival.

SUMMARY

At least in part, the present invention is based on the identification of specific tumor-derived proteins associated with circulating tumor-derived extracellular vesicles that are markers for diagnosis, staging, prognosis and response to treatment. Extracellular vesicles, released by tumors and present in the peripheral circulation of cancer patients, have been identified as important intercellular communication vehicles. The utility of circulating tumor extracellular vesicular protein components as diagnostic markers is based in part on (1) the production and release of extracellular vesicles by tumor cells and (2) the presence of specific proteins derived from the parent tumor cell associated with circulating tumor-derived extracellular vesicles. The specific tumor-derived proteins associated with circulating tumor-derived extracellular vesicles can be used as markers for diagnosis, staging, prognosis and response to treatment. Circulating extracellular vesicles have been isolated and quantitated from ovarian and lung cancer patients at various stages and grades, and compared with similar material isolated from patients diagnosed with benign ovarian or lung masses. The proteins associated with circulating tumor-derived extracellular vesicles from a set of patients (n=10/group) were profiled for 2-DIGE electrophoresis and identified by mass spectrometry to define all proteins associated with circulating extracellular vesicles. The presence of specific proteins was correlated with the presence of malignant disease versus benign disease and early versus late stage cancer. Thus, the present methods can be used for diagnosis, i.e., detection of the presence of cancer, e.g., identification and diagnosis of subjects with cancer, including distinguishing primary tumor versus metastatic tumor from a secondary site. The methods can also be used for monitoring tumor response to therapy and predicting response to therapy and overall outcome. In particular, the methods can be used to diagnose subjects with ovarian serous papillary adenocarcinoma—(Stages I and III) and non-small cell adenocarcinoma—(Stages I and III) and differentiate these from benign tumors.

In one aspect, the invention provides methods for diagnosing or assisting in diagnosing a carcinoma, e.g., an adenocarcinoma, in a subject. The methods include obtaining a sample from the subject; enriching the sample for extracellular vesicles; performing an assay to detect presence or levels of one or more proteins listed in tables 1, 3 or 5, preferably one or more proteins listed in table 5, in the extracellular vesicle-enriched sample; comparing the levels of the one or more proteins in the extracellular vesicle-enriched sample to reference levels of the one or more proteins; and diagnosing a carcinoma in a subject who has levels of the one or more proteins above the reference levels.

In another aspect, the invention features methods for diagnosing or assisting in diagnosing lung cancer in a subject. The methods include obtaining a sample from the subject; enriching the sample for extracellular vesicles; performing an assay to detect presence or levels of one or more proteins listed in table 1 in the extracellular vesicle-enriched sample; and comparing the levels of the one or more proteins in the extracellular vesicle-enriched sample to reference levels of the one or more proteins; and diagnosing lung cancer in a subject who has levels of the one or more proteins above or below reference levels, e.g., positive or negative ratios as shown in table 2.

In yet another aspect, the invention provides methods for diagnosing or assisting in diagnosing ovarian cancer in a subject, The methods include obtaining a sample from the subject; enriching the sample for extracellular vesicles; performing an assay to detect presence or levels of one or more proteins listed in table 3 in the extracellular vesicle-enriched sample; and comparing the levels of the one or more proteins in the extracellular vesicle-enriched sample to a reference level of the one or more proteins; and diagnosing an ovarian cancer in a subject who has levels of the one or more proteins above or below reference levels, e.g., positive or negative ratios as shown in table 4.

In an additional aspect, the invention provides methods for determining or assisting in determining the stage of a lung cancer in a subject. The methods include enriching the sample for extracellular vesicles; performing an assay to detect presence or levels of one or more proteins listed in table 1, e.g., a protein listed in bold in table 2, in the extracellular vesicle-enriched sample; and comparing the levels of the one or more proteins in the extracellular vesicle-enriched sample to reference levels of the one or more protein; and determining the stage of lung cancer in a subject based on a comparison with the reference levels, e.g., based on the presence of positive or negative ratios as shown in table 2.

In yet another aspect, the invention provides methods for assisting in determining the stage of ovarian cancer in a subject. The methods include enriching the sample for extracellular vesicles; performing an assay to detect presence or levels of one or more proteins listed in table 3, e.g., one or more proteins listed in bold in table 4, in the extracellular vesicle-enriched sample; and comparing the levels of the proteins in the extracellular vesicle-enriched sample to reference levels of the proteins; and determining the stage of ovarian cancer in a subject based on a comparison with the reference levels as shown in table 4, e.g., based on the presence of positive or negative ratios as shown in table 4.

In some embodiments, detecting the presence or levels of a protein in the sample comprises contacting the sample with antibodies or antigen-binding fragments thereof that bind to the protein.

In some embodiments, the subject has a mass, e.g., a mass that is suspected to be cancerous.

In some embodiments, the methods include detecting the presence of a mass in the subject. In some embodiments, detecting the mass comprises performing one or more imaging studies of the subject.

In some embodiments, the methods include administering a treatment for cancer to a subject who has been diagnosed with a carcinoma, e.g., lung cancer or ovarian cancer.

In another aspect, the invention provides methods for treating a carcinoma, e.g., an adenocarcinoma, in a subject. The methods include obtaining a sample from the subject; enriching the sample for extracellular vesicles; performing an assay to detect presence or levels of one or more proteins listed in tables 1, 3 or 5, preferably one or more proteins listed in table 5, in the extracellular vesicle-enriched sample; comparing the levels of the one or more proteins in the extracellular vesicle-enriched sample to reference levels of the one or more proteins; diagnosing a carcinoma in a subject who has levels of the one or more proteins above the reference levels; and administering a treatment for carcinoma to the subject.

In yet another aspect, the invention provides methods for treating lung cancer in a subject. The methods include obtaining a sample from the subject; enriching the sample for extracellular vesicles; performing an assay to detect presence or levels of one or more proteins listed in table 1 in the extracellular vesicle-enriched sample; comparing the levels of the one or more proteins in the extracellular vesicle-enriched sample to reference levels of the one or more proteins; diagnosing lung cancer in a subject who has levels of the one or more proteins above or below reference levels, e.g., positive or negative ratios as shown in table 2; and administering a treatment for lung cancer to the subject.

In yet another aspect, the invention provides methods for treating ovarian cancer in a subject. The methods include obtaining a sample from the subject; enriching the sample for extracellular vesicles; performing an assay to detect presence or levels of one or more proteins listed in table 3 in the extracellular vesicle-enriched sample; and comparing the levels of the one or more proteins in the extracellular vesicle-enriched sample to a reference level of the one or more proteins; diagnosing a ovarian cancer in a subject who has levels of the one or more proteins above or below reference levels, e.g., positive or negative ratios as shown in table 4; and administering a treatment for ovarian cancer to the subject.

In some embodiments of the methods described herein, the treatment comprises one or more of surgical treatment (e.g., resection or debulking), chemotherapy, immunotherapy, or radiotherapy, as is known in the art and/or described herein.

Also provided are kits that contain one or more antibodies that bind to a biomarker of cancer as described herein. In some embodiments of the kits described herein, the kit is an enzyme-linked immunosorbent assay. Any of the kits described herein can be used to perform any of the methods described herein. In some embodiments, the kits can further include instructions for performing any of the methods described herein.

In some embodiments of the methods described herein, the methods include comparing a detected level of a protein biomarker to a reference level. In some embodiments, the reference represents levels of the biomarkers in a healthy control, i.e., a subject who has not been diagnosed with cancer. In some embodiments of the methods described herein, the reference level represents levels of the biomarkers in a cancer control subject, i.e., a subject diagnosed with a cancer, e.g., a carcinoma, adenocarcinoma, lung cancer or ovarian cancer. In certain embodiments, the cancer control is from a subject having lung cancer or ovarian cancer. In some embodiments, the reference level is a median or cutoff level in a reference cohort, e.g., a cutoff defining a statistically significantly distinct group, e.g., a top or bottom tertile, quartile, quintile, or other percentile of the reference cohort.

Depending on the identity of the protein biomarker detected, levels above or below the reference level may be indicative of the presence of disease or increased risk; whether increased levels (i.e., levels above the reference) or decreased levels (i.e., levels below the reference) indicate the presence of disease or decreased risk can be readily determined from tables 2 and 4.

In some embodiments, levels above a reference level are statistically significant increased, or by at least 5%, 10%, 15%, 20%, 25%, 30%, 35%, 40%, 45%, 50%, 55%, 60%, 65%, 70%, 75%, 80%, 85%, 90%, 95%, 100%, 200%, 300%, 400%, 500%, or 1000%. An increase, as described herein, can be determined by comparison to a threshold or baseline value (e.g., a threshold detection level of an assay for determining the presence or absence of a protein, or a reference level of protein in a reference subject (e.g., healthy reference or a subject who has cancer, e.g., a known stage of cancer). In some embodiments, levels below a reference level are statistically significant decreased, or by at least 5%, 10%, 15%, 20%, 25%, 30%, 35%, 40%, 45%, 55%, 60%, 65%, 70%, 75%, 80%, 85%, 90%, or 95%. A decrease, as described herein, can be determined by comparison to a threshold or baseline value (e.g., a threshold detection level of an assay for determining the presence or absence of a protein, or a level of protein in a reference subject (e.g., a healthy reference subject or a subject who does not have cancer, e.g., does not have lung or ovarian cancer).

In some embodiments, the methods include calculating a ratio of the level of the protein biomarker in the subject sample to a reference level, and if the ratio is greater than a threshold ratio, determining that the subject has or is at risk of developing a carcinoma as described herein, e.g., adenocarcinoma, e.g., lung or ovarian cancer. In some embodiments, whether the ratio is positive or negative is determined and the presence of a positive or negative ratio indicates that the subject has or is at risk of developing a carcinoma as described herein, e.g., adenocarcinoma, e.g., lung or ovarian cancer. Again, whether a positive or negative ratio indicate the presence of disease or decreased risk can be readily determined from tables 2 and 4.

As used herein, a "subject" is a vertebrate, including any member of the class mammalia, including humans, domestic and farm animals, and zoo, sports or pet animals, such as mouse, rabbit, pig, sheep, goat, cattle, horse (e.g., race horse), and higher primates. In preferred embodiments, the subject is a human.

By the term "detecting" is meant measuring or identifying the presence of any portion of a molecule (e.g., peptide or protein) in a sample (e.g., an extracellular vesicle enriched sample). Detecting, as described herein, can include identifying or measuring the presence or absence of one or more peptides or proteins having at least 10 (e.g., at least 11, 12, 13, 14, 15, 16, 17, 18, 19, 20, or 25) contiguous amino acids of a biomarker of cancer as described herein in a sample. Exemplary proteins that can be detected contain at least 10 (e.g., at least 11, 12, 13, 14, 15, 16, 17, 18, 19, 20, or 25) contiguous amino acids of a sequence within a biomarker of cancer as described herein. The contiguous amino acid sequence can be present within any portion of the sequence of a biomarker of cancer as described herein, for example, a sequence starting at the N-terminus, a sequence ending at the C-terminus, or a sequence starting at any single amino acid within the sequence (with the exception of the last four amino acids at the C-terminus of the protein.

By the term "extracellular vesicle" is meant a lipid-based microparticle or nanoparticle, or protein-rich aggregate, present in a sample (e.g., a biological fluid) obtained from a subject. Extracellular vesicles are also referred to in the art and herein as exosomes, microvesicles or nanovesicles. In the present disclosure, an extracellular vesicle is between about 20 nm to about 90 nm in diameter. Extracellular vesicles are secreted or shed from a variety of different mammalian cell types. Non-limiting examples of extracellular vesicles and methods for the enrichment of extracellular vesicles from a sample (e.g., a biological fluid) obtained from a mammalian subject are described herein. Additional examples of extracellular vesicles and methods for the enrichment of extracellular vesicles from a sample obtained from a mammalian subject are known in the art.

By the term "sample" or "biological sample" is meant any biological fluid obtained from a mammalian subject (e.g., composition containing blood, plasma, serum or other blood fractions, lymph, urine, cerebrospinal fluid, ascites, saliva, breast milk, tears, vaginal discharge, amniotic fluid, lavage, semen, glandular secretions, exudate, contents of cysts and feces). In preferred embodiments, the sample comprises blood, serum, or plasma.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1A:
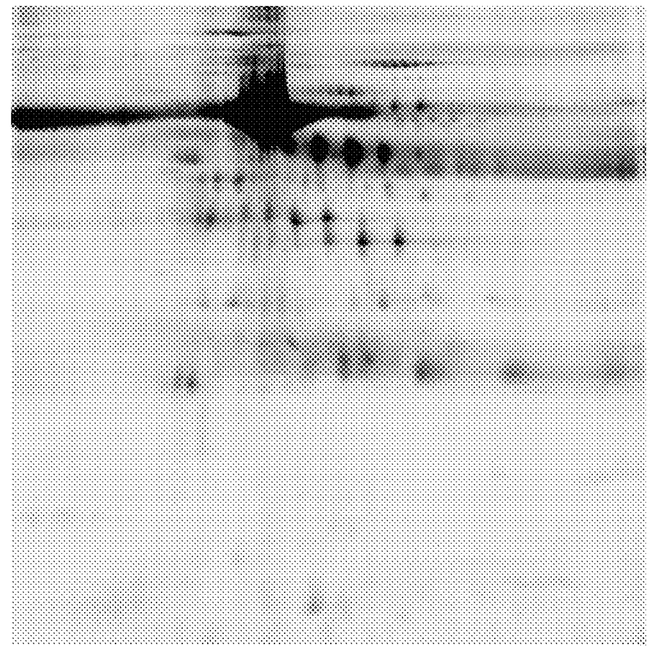
FIGS. 1A-C are images showing the results of 2DIGE analysis of proteins in extracellular vesicle-enriched samples from subjects with benign (1A), stage I (1B), and stage III (1C) lung disease.

Described herein is the identification of specific tumor-derived proteins associated with circulating tumor-derived extracellular vesicles as markers for diagnosis, staging, prognosis and response to treatment in lung and ovarian cancer. The present inventors have isolated and quantitated circulating extracellular vesicles from ovarian and lung cancer patients at various stages and grades and compared them with similar material isolated from patients diagnosed with benign ovarian or lung masses. The proteins associated with circulating tumor-derived extracellular vesicles from a set of patients were profiled for 2-DIGE electrophoresis and identified by mass spectrometry to define all proteins associated with circulating extracellular vesicles. The presence of specific proteins correlated with the presence of malignant disease versus benign disease and early versus late stage lung or ovarian cancers.

Thus, the present methods can be used to detect the presence of epithelial tumors, e.g., lung or ovarian cancer, or to stage lung or ovarian cancer.

Epithelial Cancer

The methods described herein can be used to diagnose the presence of, and determine the stage of, cancer, i.e., carcinomas, e.g., solid tumors of epithelial tissues or of epithelial origin, in a subject. Carcinomas are divided into two major subtypes: adenocarcinoma, which develops in an organ or gland, and squamous cell carcinoma, which originates in the squamous epithelium. In some embodiments, the methods described herein can be used to diagnose and/or stage adenocarcinoma in a subject. Examples include skin, pancreatic (e.g., pancreatic ductal adenocarcinoma), stomach, lung, esophagus, throat, breast, renal, hepatic, bile duct, urogenital (e.g., bladder, prostate, urachus, vaginal, cervical), ovarian, or colon cancer.

As used herein, the term "hyperproliferative" refer to cells having the capacity for autonomous growth, i.e., an abnormal state or condition characterized by rapidly proliferating cell growth. Hyperproliferative disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. A "tumor" is an abnormal growth of hyperproliferative cells. "Cancer" refers to pathologic disease states, e.g., characterized by malignant tumor growth.

Table 5 lists extracellular vesicle-associated proteins that identified samples with both lung and ovarian cancer; these proteins can thus be used to diagnose the presence of cancers of epithelial origin.

Lung Cancer

Lung cancer is the leading cause of cancer deaths among men and women in the United States (Jemal et al., CA Cancer J. Clin. 2004 January-February; 54(1):8-29). Clinical treatment has not resulted in major increases in survival rates (Shi et al., BMC Cancer. 2011; 11: 92); early and accurate detection is key to improving survival.

Extracellular vesicle-associated proteins that are associated with the presence of lung cancer are listed herein in Table 1. Associations of these proteins with a certain stage of lung cancer are shown herein in Table 2.

Ovarian Cancer

While ovarian cancer accounts for only one third of gynecologic cancers, it results in 55% of deaths from gynecologic malignancies and 6% of all cancer deaths in women (Memarzadeh and Berek, J Reprod Medicine 2001, 46:621-629; Hoskins, J Cell Biochem 1995; 23 (suppl): 189-199). Long-term survival has not changed significantly in the last three decades, largely due to inadequate diagnostic approaches that only detect well-established cancers. Only 19% of ovarian cancers are diagnosed at Stage I (Hoskins, J Cell Biochem 1995, 23 (suppl): 189-199), while other cancers associated with women are primarily diagnosed at Stage I (77% of endometrial cancers, 55% of breast cancers and 83% of cervical cancers). Since Stage I ovarian cancer can be cured in 90% of cases, but five-year survival for advanced disease (Stage III and IV) is less than 21%, prospects for significant improvement in survival reside in early diagnosis of disease.

Extracellular vesicle-associated proteins that are associated with the presence of ovarian cancer are listed herein in Table 3. Associations of these proteins with a certain stage of ovarian cancer are shown in Table 4.

Methods for Diagnosing and Staging Cancer

Included herein are methods for diagnosing and staging carcinoma, e.g., ovarian or lung cancer. In any of the methods described herein, the level, presence or absence of one or more (e.g., one, two, three, four, five, six, seven, eight, nine, ten, eleven, or twelve) of the biomarkers described herein is determined in a sample from the subject. The presence and/or level of a protein indicates the presence or stage of an epithelial cancer, e.g., lung or ovarian cancer in a subject. Thus the methods can include the detection of the presence or levels of the proteins in a sample comprising extracellular vesicles. The methods described herein can also be used for distinguishing primary tumor versus metastatic tumor from a secondary site; monitoring tumor response to therapy; and predicting response to therapy and overall outcome. The present methods typically include enriching the sample for extracellular vesicles before detecting the presence or levels of the proteins.

Some embodiments further include updating a subject's clinical records to indicate the diagnosis or the determined stage of cancer. Some embodiments further include performing one or more additional clinical tests for a cancer (e.g., ovarian or lung cancer). Some embodiments further include administering a treatment (e.g., any of the treatments described herein or known in the art) to a subject identified as having cancer or a subject identified as having a specific stage of cancer (e.g., a subject having stage I, II, or III of cancer, e.g., ovarian or lung cancer). Some embodiments further include performing exploratory surgery to resect the cancer from a subject identified as having a cancer (e.g., ovarian or lung cancer) or a subject identified as having a specific stage of cancer (e.g., a subject identified as having stage I, II, or III cancer, e.g., ovarian or lung cancer). Some embodiments further include modifying a computer database to indicate the subject's diagnosis with a cancer or the subject's stage of cancer.

In some embodiments, the subject is suspected of having a cancer (e.g., ovarian or lung cancer) or has an increased risk of developing a cancer (e.g., ovarian or lung cancer). For example, a subject having an increased risk of developing a cancer can have one or more lineal family members that have been diagnosed with the specific type of cancer or have had one or more environmental exposures that are thought to contribute to the pathogenesis of a cancer (e.g., exposure to cigarette smoke, herbicides, or other mutagens). In the methods of staging a cancer, the subject may have previously been diagnosed with a cancer (e.g., an early form of cancer) (e.g., ovarian or lung cancer). The presence and/or level of a protein can be evaluated using methods known in the art, e.g., using quantitative immunoassay methods. In some embodiments, high throughput methods, e.g., protein or gene chips as are known in the art (see, e.g., Ch. 12, Genomics, in Griffiths et al., Eds. Modern genetic Analysis, 1999, W. H. Freeman and Company; Ekins and Chu, Trends in Biotechnology, 1999, 17:217-218; MacBeath and Schreiber, Science 2000, 289 (5485):1760-1763; Simpson, Proteins and Proteomics: A Laboratory Manual, Cold Spring Harbor Laboratory Press; 2002; Hardiman, Microarrays Methods and Applications: Nuts & Bolts, DNA Press, 2003), can be used to detect the presence and/or level of proteins.

In an exemplary clinical decision tree of cancer, there are three potential points for applying biomarkers, such as tumor-reactive antibodies. First, potential biomarkers can be used for screening by applying them to the detection of cancer in asymptomatic individuals in high risk populations or in the general population. Second, potential biomarkers can be used for definitive diagnosis of individuals with suspicious or palpable masses, ultrasound-identified masses or symptoms of pelvic or abdominal pain. Third, potential biomarkers can be used for disease monitoring or follow-up in individuals treated for ovarian cancer (by surgery and first-line chemotherapy) to assess the therapeutic responses of residual and metastatic disease and for early identification of recurrence. The biomarkers described herein can be used at one or more, or all three, of the above, or at other time points, e.g., as determined by a health care provider or insurance provider.

Sample Preparation and Assay Methods

In any of the methods described herein, the level, presence or absence of one or more (e.g., one, two, three, four, five, six, seven, eight, nine, ten, eleven, twelve or more) of the biomarkers described herein is determined in a sample from the subject.

A sample (e.g., a sample containing a biological fluid, selected from the group consisting of blood, serum, plasma or other blood fractions, lymph, urine, cerebrospinal fluid, ascites, saliva, lavage, semen, glandular secretions, exudate, contents of cysts and feces) can be collected from a subject (e.g., any of the subjects described herein, such as a mammalian subject, preferably a human subject) at any time, e.g., during a routine annual physical, during an evaluation specifically to detect possible malignancy, or during an evaluation to stage a previously identified malignancy. Samples can be used immediately or frozen or stored for a period of time (e.g., at least one day, two days, three days, four days, five days, six days, 1 week or several months) prior to detecting/determining the presence or absence of one or more biomarkers as described herein.

Preferably, the sample will be enriched for extracellular vesicles, e.g., using a method described herein or known in the art.

The sample can be extracted using Trizol following the manufacturer's instructions to remove RNA. After the RNA removal step, protein isolation from extracellular vesicles can be performed, for example, by continuing the TRIZOL isolation procedure, as described by the manufacturer, preferably with subsequent washing and other cleanup steps for SDS gel analysis or LCMS preparation. In some embodiments, the quantity of protein can be determined by the Bradford microassay method, using BSA as a standard. Any protein isolation methods described herein or known in the art can be used.

Any method known in the art can be used for detecting the presence of proteins (e.g., using one or more antibodies that specifically bind to a biomarker as described herein). For example, a sample can be contacted with one or more antibodies or antigenic portions thereof that specifically bind to a biomarker as described herein; the binding of the one or more antibodies to proteins present in the sample can be detected using methods known in the art.

In some embodiments of the methods described herein, an array (e.g., any array, microarray, biochip, or point-of-care test as is known in the art) can be provided that comprises one or more antibodies that specifically bind to a biomarker as described herein, and the array can be contacted with the sample (e.g., a sample containing a biological fluid, e.g., serum or plasma) from the subject, and the binding of any proteins present in the sample can be detected. Methods for detecting binding of the antibodies to target proteins are known in the art, and can include the use of secondary antibodies. The secondary antibodies are generally modified to be detectable, e.g., labeled. The term "labeled" is intended to encompass direct labeling by coupling (i.e., physically linking) a detectable substance to the secondary antibody, as well as indirect labeling of the multimeric antigen by reactivity with a detectable substance. Examples of detectable substances include various enzymes, prosthetic groups, fluorescent materials, luminescent materials, bioluminescent materials, and radioactive materials. Examples of suitable enzymes include horseradish peroxidase (HRP), alkaline phosphatase, β-galactosidase, and acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, and quantum dots, dichlorotriazinylamine fluorescein, dansyl chloride, and phycoerythrin; an example of a luminescent material includes luminol; examples of bioluminescent materials include green fluorescent protein and variants thereof, luciferase, luciferin, and aequorin; and examples of suitable radioactive material include $^{125}I$, $^{131}I$, $^{35}S$, or $^{3}H$. Methods for producing such labeled antibodies are known in the art, and many are commercially available.

Any method of detecting proteins present in a sample can be used, including but not limited to radioimmunoassays (RIA), enzyme-linked immunosorbent assays (ELISA), Western blotting, surface plasmon resonance, micro fluidic devices, protein array, protein purification (e.g., chromatography, such as affinity chromatography), mass spectrometry, two-dimensional gel electrophoresis, or other assays as known in the art.

The term "array," as used herein, generally refers to a predetermined spatial arrangement of binding ligands (e.g., antibodies or nucleic acid probes) or spatial arrangements of binding ligands or antigens. Arrays according to the present invention include antibodies or nucleic acid probes immobilized on a surface may also be referred to as "antibody arrays" or "gene arrays," respectively. Arrays according to the present invention that comprise surfaces activated, adapted, prepared, or modified to facilitate the binding of sample proteins or nucleic acids to the surface may also be referred to as "binding arrays." Further, the term "array" can be used herein to refer to multiple arrays arranged on a surface, such as would be the case where a surface bore multiple copies of an array. Such surfaces bearing multiple arrays may also be referred to as "multiple arrays" or "repeating arrays." The use of the term "array" herein can encompass antibody arrays, gene arrays, binding arrays, multiple arrays, and any combination thereof; the appropriate meaning will be apparent from context. An array can include antibodies that detect proteins altered in a subject who cancer or a specific stage of cancer. The array can be contacted with one or more samples from a subject.

An array of the invention comprises a substrate. By "substrate" or "solid support" or other grammatical equivalents, herein is meant any material appropriate for the attachment of antibodies or nucleic acid probes and is amenable to at least one detection method. As will be appreciated by those in the art, the number of possible substrates is very large. Possible substrates include, but are not limited to, glass and modified or functionalized glass, plastics (including acrylics, polystyrene, and copolymers of styrene and other materials, polypropylene, polyethylene, polybutylene, polyurethanes, TEFLON®, etc.), polysaccharides, nylon or nitrocellulose, resins, silica or silica-based materials including silicon and modified silicon, carbon, metals, inorganic glasses, plastics, ceramics, and a variety of other polymers. In addition, as is known the art, the substrate can be coated with any number of materials, including polymers, such as dextrans, acrylamides, gelatins, or agarose. Such coatings can facilitate the use of the array with a sample derived from a biological fluid, e.g., urine, plasma, or serum.

A planar array will generally contain addressable locations (e.g., "spots," "pads," "addresses," or "micro-locations") of antibodies or nucleic acid probes in an array format. The size of the array will depend on the composition and end use of the array. The arrays can contain one, two, or more different antibodies or nucleic acid probes. Generally, the array will comprise from two to as many as 20 different antibodies or nucleic acid probes, depending on the end use of the array. A microarray of the invention will generally comprise at least one antibody or nucleic acid probe that identifies or "captures" a target protein or nucleic acid present in a biological sample. In some embodiments, in some arrays, multiple substrates can be used, either of different or identical compositions. Thus, for example, large planar arrays can comprise a plurality of smaller substrates.

As an alternative to planar arrays, bead-based assays in combination with flow cytometry have been developed to perform multiparametric immunoassays. In bead-based assay systems, one or more antibodies can be immobilized on addressable microspheres. Each antibody for each individual immunoassay is coupled to a distinct type of microsphere (i.e., "microbead") and the immunoassay reaction takes place on the surface of the microspheres. Dyed microspheres with discrete fluorescence intensities are loaded separately with their appropriate biomolecules. The different bead sets carrying different capture probes (e.g., antibodies) can be pooled as necessary to generate custom bead arrays. Bead arrays are then incubated with the sample in a single reaction vessel to perform the immunoassay.

In some embodiments, product formation of the target protein with an antibody can be detected with a fluorescence-based reporter system. The antibodies can be labeled directly by a fluorogen or detected by a second fluorescently-labeled capture biomolecule. The signal intensities derived from target-bound antibodies are measured in a flow cytometer. The flow cytometer first identifies each microsphere by its individual color code. Second the amount of antibody on each individual bead is measured by the second color fluorescence specific for the bound target. This allows multiplexed quantitation of multiple targets from a single sample within the same experiment. Sensitivity, reliability, and accuracy are comparable to standard microtiter ELISA procedures. With bead-based immunoassay systems, proteins can be simultaneously quantified from biological samples. An advantage of bead-based systems is the individual coupling of an antibody to distinct microspheres.

Thus, microbead array technology can be used to sort proteins bound to specific antibodies using a plurality of microbeads, each of which can carry about 100,000 identical molecules of a specific antibody on its surface. Once captured, the protein can be handled as a fluid, referred to herein as a "fluid microarray."

An array can encompass any means for detecting a protein. For example, microarrays can be biochips that provide high-density immobilized arrays of antibodies, where antibody binding is monitored indirectly (e.g., via fluorescence). In addition, an array can be of a format that involves the capture of target proteins by biochemical or intermolecular interaction, coupled with direct detection, e.g., by mass spectrometry (MS), e.g., LC-MS or HPLC-MS.

Arrays and microarrays that can be used with the methods described herein can be made according to the methods described in U.S. Pat. Nos. 6,329,209; 6,365,418; 6,406,921; 6,475,808; and 6,475,809, which are incorporated herein in their entirety. New arrays, to detect specific selections or sets of biomarkers described herein can also be made using the methods described in these patents.

The antibodies can be immobilized on the surface using methods and materials that minimize the denaturing of the antibodies, that minimize alterations in the structure of the antibodies, or that minimize interactions between the antibodies and the surface on which they are immobilized.

Surfaces useful in the arrays can be of any desired shape (form) and size. Non-limiting examples of surfaces include chips, continuous surfaces, curved surfaces, flexible surfaces, films, plates, sheets, tubes, and the like. Surfaces preferably have areas ranging from approximately a square micron to approximately 500 $cm^2$. The area, length, and width of surfaces according to the present invention can be varied according to the requirements of the assay to be performed. Considerations may include, for example, ease of handling, limitations of the material(s) of which the surface is formed, requirements of detection systems, requirements of deposition systems (e.g., arrayers), and the like.

In certain embodiments, it is desirable to employ a physical means for separating groups or arrays of binding islands or immobilized antibodies or nucleic acid probes: such physical separation facilitates exposure of different groups or arrays to different solutions of interest. Therefore, in certain embodiments, arrays are situated within wells of 96-, 384-, 1536-, or 3456-microwell plates. In such embodiments, the bottoms of the wells can serve as surfaces for the formation of arrays, or arrays can be formed on other surfaces and then placed into wells. In certain embodiments, such as where a surface without wells is used, binding islands can be formed or antibodies or nucleic acid probes can be immobilized on a surface and a gasket having holes spatially arranged so that they correspond to the islands or antibodies/nucleic acid probes can be placed on the surface. Such a gasket is preferably liquid-tight. A gasket can be placed on a surface at any time during the process of making the array and can be removed if separation of groups or arrays is no longer necessary.

The immobilized antibodies or nucleic acid probes can bind to proteins or nucleic acids present in a biological sample overlying the immobilized antibodies/nucleic acid probes. For example, a target protein or nucleic acid present in a biological sample can contact an immobilized antibody or nucleic acid probe and bind to it, thereby facilitating detection of the target protein or nucleic acid.

Modifications or binding of target proteins to antibodies in solution or immobilized on an array can be detected using detection techniques known in the art. Examples of such techniques include immunological techniques such as competitive binding assays and sandwich assays; fluorescence detection using instruments such as confocal scanners, confocal microscopes, or CCD-based systems, and techniques such as fluorescence, fluorescence polarization (FP), fluorescence resonant energy transfer (FRET), total internal reflection fluorescence (TIRF), fluorescence correlation spectroscopy (FCS); colorimetric/spectrometric techniques; surface plasmon resonance, by which changes in mass of materials adsorbed at surfaces can be measured; techniques using radioisotopes, including conventional radioisotope binding and scintillation proximity assays (SPA); mass spectroscopy, such as liquid chromatography-mass spectrometry (LC-MS), HPLC-MS, matrix-assisted laser desorption/ionization mass spectroscopy (MALDI) and MALDI-time of flight (TOF) mass spectroscopy; ellipsometry, which is an optical method of measuring thickness of protein films; quartz crystal microbalance (QCM), a very sensitive method for measuring mass of materials adsorbing to surfaces; scanning probe microscopies, such as atomic force microscopy (AFM) and scanning electron microscopy (SEM); and techniques such as electrochemical, impedance, acoustic, microwave, and infrared (IR)/Raman detection. See, e.g., Mere et al., "Miniaturized FRET assays and microfluidics: key components for ultra-high-throughput screening," *Drug Discovery Today* 4(8):363-369, 1999, and references cited therein; Lakowicz, Principles of Fluorescence Spectroscopy, 2nd Edition, Plenum Press, 1999.

Arrays as described herein can be included in kits. Such kits can also include, as non-limiting examples, one or more of: reagents useful in preparing a sample, reagents useful for enriching extracellular vesicles, reagents useful for detecting binding of target proteins or nucleic acids in a sample to immobilized antibodies, control samples that include purified target proteins, and/or instructions for use.

For example, kits useful in the methods described herein can include one or more (e.g., two, three, four, five, six, seven, eight, nine, ten, eleven, twelve, thirteen, fourteen, or fifteen) antibodies or fragments thereof that specifically bind to a biomarker as described herein. For example, the one or more antibodies provided in the kits can be immobilized on a surface (e.g., in the form of an ELISA assay or a gene-chip array).

Enriching Extracellular Vesicles

Any of the methods described herein can include enriching extracellular vesicles from the sample, wherein the presence or absence of one or more of the biomarkers described herein in the enriched extracellular vesicles is determined (e.g., using any of the methods described herein). A sample that is enriched in extracellular vesicles need not be 100% pure extracellular vesicles.

Extracellular vesicles can be enriched using any methods known in the art (see, for example the techniques described in Taylor et al., Serum/Plasma Proteomics, Chapter 15, "Extracellular vesicle Isolation for Proteomic Analyses and RNA Profiling," Springer Science, 2011; and Tauro et al., Methods 56 (2012) 293-304, and references cited therein). Extracellular vesicles can be enriched from a biological fluid from a subject, e.g., blood, plasma, serum, or ascites. In some embodiments, for the enrichment of extracellular vesicles from blood, serum, or plasma using centrifugation, sodium heparin (1,000 m/L), sodium citrate or potassium citrate can be added prior to isolation and the blood can be centrifuged at 12,000×g for 15 min at 4° C. to remove any cellular debris.

The cell-free blood specimens can further be centrifuged at 100,000×g for 1 h at 4° C. The pellet containing extracellular vesicles can be resuspended in PBS, and recentrifuged at 100,000×g for 1 h at 4° C. The resulting extracellular vesicle pellet can be used for TRIZOL extraction for RNA and protein determination (using any of the methods described herein).

In some embodiments, extracellular vesicles can also be enriched using size exclusion chromatography or affinity purification. In an exemplary method, 2 mL aliquots of patient-derived cell-free ascites or serum can be applied to a 2% agarose-based gel column (2.5×16 cm). For optimal separation, the sample volume should be 1/20 of the total column volume (as defined by $\Pi^2h$). The column can be eluted isocratically with PBS (e.g., at a flow rate of 1 mL/min), or other diluents such as modified PBS or water (e.g., distilled deionized water ($DDH_2O$), while monitoring absorbance at 280 nm, and collecting fractions (2 mL). The void volume fractions (based on absorbance at 280 nm) can be pooled and centrifuged at 100,000×g for 1 hour at 4° C. The resulting pellet (containing extracellular vesicles) can be used for TRIZOL extraction for RNA and protein analyses (using any of the methods described herein).

In some embodiments, extracellular vesicles can also be enriched using magnetic beads. In an exemplary method, serum can be absorbed to selected antibodies such as anti-EpCAM antibodies coupled to magnetic microbeads. Anti-EpCAM coupled to microbeads (50 mL) can be added to the serum specimens (2 mL), mixed, and incubated on a shaker for 2 h at room temperature. Each tube is thereafter placed in the magnetic separator and fluid removed, leaving the magnetic beads and the bound extracellular vesicles attached to the side of the tube. The tube is then removed from the magnetic separator and the beads rinsed with 500 mL TBS, and the separation repeated. After the wash step, the tube is removed from the magnetic holder and the bead/extracellular vesicle complex can be used for TRIZOL extraction for RNA and protein analyses (using any of the methods described herein).

In some embodiments, extracellular vesicles can also be enriched using precipitation. In one exemplary method, the specimen (2 mL ascites or serum) is transferred to a sterile tube and 0.5 mL ExoQuick extracellular vesicle precipitation solution can be added and mixed. The mixture is then incubated overnight (at least 12 hours) at 4° C. and the mixture subsequently centrifuged at 10,000×g in a microfuge for 5 minutes at 4° C. The supernatant is aspirated and the extracellular vesicle pellet can be extracted using the TRIZOL extraction procedures for protein and RNA analyses (using any of the methods described herein).

Alternatively, samples can be centrifuged, e.g., at 400 g for 10 min, and the supernatant then centrifuged again, e.g., at 10,000 g for 20 min. The supernatant is applied to a column, e.g., a Sepharose 2B column (1.0×15 cm), and the sample fractionated isocratically, e.g., with Tris-buffered saline (TBS). The elution can be monitored, e.g., by absorbance at 280 nm, and the void volume fractions, containing material greater than 50,000,000 Da, collected and pooled. This material is concentrated, e.g., by ultrafiltration, e.g., using an Amicon 8400 stirred cell with a 500,000-Da cutoff membrane. The protein quantities of the concentrated vesicular fractions can be determined, e.g., using a Bradford microassay method (Bio-Rad, Hercules, Calif., USA), e.g., using bovine serum albumin as a standard.

In some embodiments, the proteins can be further fractionated using 2D-difference gel electrophoresis (DIGE). An exemplary method is as follows. The vesicular proteins (e.g., about 100 μg) are labeled; when comparison of two classes of extracellular vesicles (e.g., patient-derived and control (normal subject) vesicles is desired, the vesicles can be differentially labeled, e.g., with Cy2 and Cy3. 2D-DIGE analysis is then performed. Labeled samples (100 μg each) are applied to immobilized pH gradient strips. After isoelectric focusing, the strips are incubated in equilibration buffer. The strips are placed on polyacrylamide gels, cast using low fluorescence glass plates. After electrophoretic separation, individual images of labeled proteins are obtained e.g., using a scanner with appropriate excitation/emission wavelengths, e.g., 480 nm/530 nm for Cy2 and 520 nm/590 nm for Cy3. The 2D-DIGE gels can be evaluated using suitable software, e.g., DeCyder™ 6.0 software. Statistical analysis and comparisons can be performed, e.g., using the Biological Variation Analysis module (GE Healthcare). Protein spots can be excised and processed for confirmation of identity, e.g., by tandem mass spectrometry (MS).

Methods of Treatment

In some embodiments, the methods described herein can be used to treat a subject, e.g., to select a subject for treatment. In some embodiments, the methods described herein include the administration of a treatment for cancer to a subject who has been selected or identified as having cancer by a method described herein. Such treatments are known in the art and include surgical treatment (e.g., resection or debulking), chemotherapy, immunotherapy, radiotherapy, and others.

Examples of chemotherapeutics include, without limitation, an antimetabolite, an alkylating agent, interleukin-2, or a therapeutic antibody. Non-limiting examples of antimetabolites include methotrexate, trimetrexate, pentostatin, cytarabine, fludarabine phosphate, hydroxyurea, fluorouracil, floxuridine, chlorodeoxyadenosine, gemcitabine, thioguanine, and 6-mercaptopurine. Non-limiting examples of alkylating agents include lomustine, carmustine, streptozocin, mechlorethamine, melphalan, uracil nitrogen mustard, chlorambucil, cyclophosphamide, iphosphamide, cisplatin, carboplatin, mitomycin, thiotepa, dacarbazin, procarbazine, hexamethyl melamine, triethylene melamine, busulfan, pipobroman, and mitotane. Non-limiting examples of therapeutic antibodies include ipilimumab and trastuzumab. Additional exemplary cancer therapeutics include bleomycin, topotecan, irinotecan, camptothecin, daunorubicin, doxorubicin, idarubicin, mitoxantrone, teniposide, etoposide, dactinomycin, mithramycin, vinblastine, vincristine, navelbine, paclitaxel, and docetaxel. In some embodiments, a subject is identified as having cancer using a method described herein and administered a cancer therapeutic selected from the group of doxorubicin and topotecan.

The dosage and selection of the therapeutic treatment can be determined by a health care professional based on known in the art. See, e.g., Abraham et al., The Bethesda Handbook of Clinical Oncology (Lippincott Williams & Wilkins; Third edition, Sep. 4, 2009); Casciato and Territo, Manual of Clinical Oncology (Lippincott Manual Series) (Lippincott Williams & Wilkins; Sixth, North American Edition, Sep. 5, 2008); Haffly and Wilson, Handbook of Radiation Oncology Basic Principles and Clinical Protocols, (Jones & Bartlett Publishers; 1st edition, Jul. 23, 2008); and Abeloff et al., Abeloffs Clinical Oncology: Expert Consult (Churchill Livingstone; 4 edition, May 21, 2008); Feig et al., The M.D. Anderson Surgical Oncology Handbook (Lippincott Williams & Wilkins; Fourth edition (Jun. 21, 2006).

EXAMPLES

The invention is further described in the following examples, which do not limit the scope of the invention described in the claims.

Example 1

Extracellular Vesicle-Associated Proteins in Ovarian and Lung Cancer

This example describes differential extracellular vesicle-associated protein profiles that distinguish benign, Stage I and Stage III cancers.

The cancers evaluated included Ovarian (ovarian serous papillary adenocarcinoma—stages I and III, and ovarian adenoma (benign)) and Lung (non-small cell adenocarcinoma—stages I and III, and benign lung disease).

Extracellular vesicles were isolated chromatographically as follows. 2 mL aliquots of patient-derived cell-free ascites or serum were applied to a 2% agarose-based gel column (2.5×16 cm). The column was eluted isocratically with PBS (at a flow rate of 1 mL/min). Absorbance was monitored at 280 nm and fractions (2 mL) were collected. The void volume fractions (based on absorbance at 280 nm) were pooled and centrifuged at 100,000×g for 1 hour at 4° C. The pellet (containing extracellular vesicles) was subjected to TRIZOL extraction.

The resulting protein fractions from three patients within each group were pooled and were subjected to 2DIGE, following labeling with a different Cy label (Benign was labeled with Cy3). Labeled samples (100 μg each) were applied to immobilized pH gradient strips. After isoelectric focusing, the strips were incubated in equilibration buffer. The strips were placed on polyacrylamide gels, cast using low fluorescence glass plates. After electrophoretic separation, individual images of Cy2- and Cy3-labeled proteins were obtained using a Typhoon 94100 scanner with excitation/emission wavelengths of 480 nm/530 nm for Cy2 and 520 nm/590 nm for Cy3. To define proteins exhibiting differential expression, 2D-DIGE gels were evaluated with DeCyder 6.0 software using pair-wise comparisons.

Figure 1B:
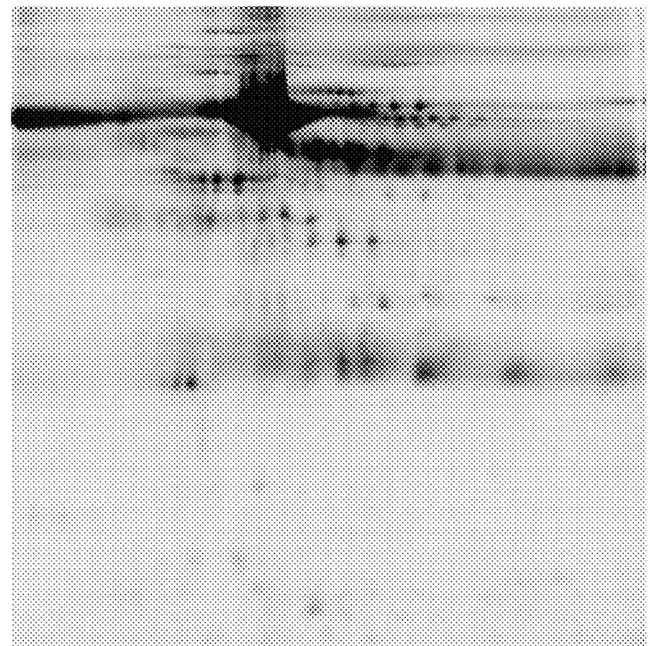
Figure 1C:
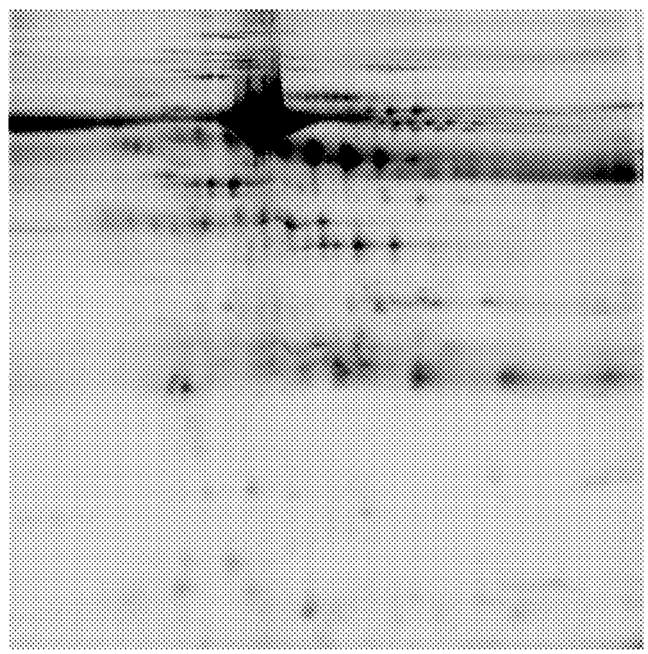
Figure 1D:
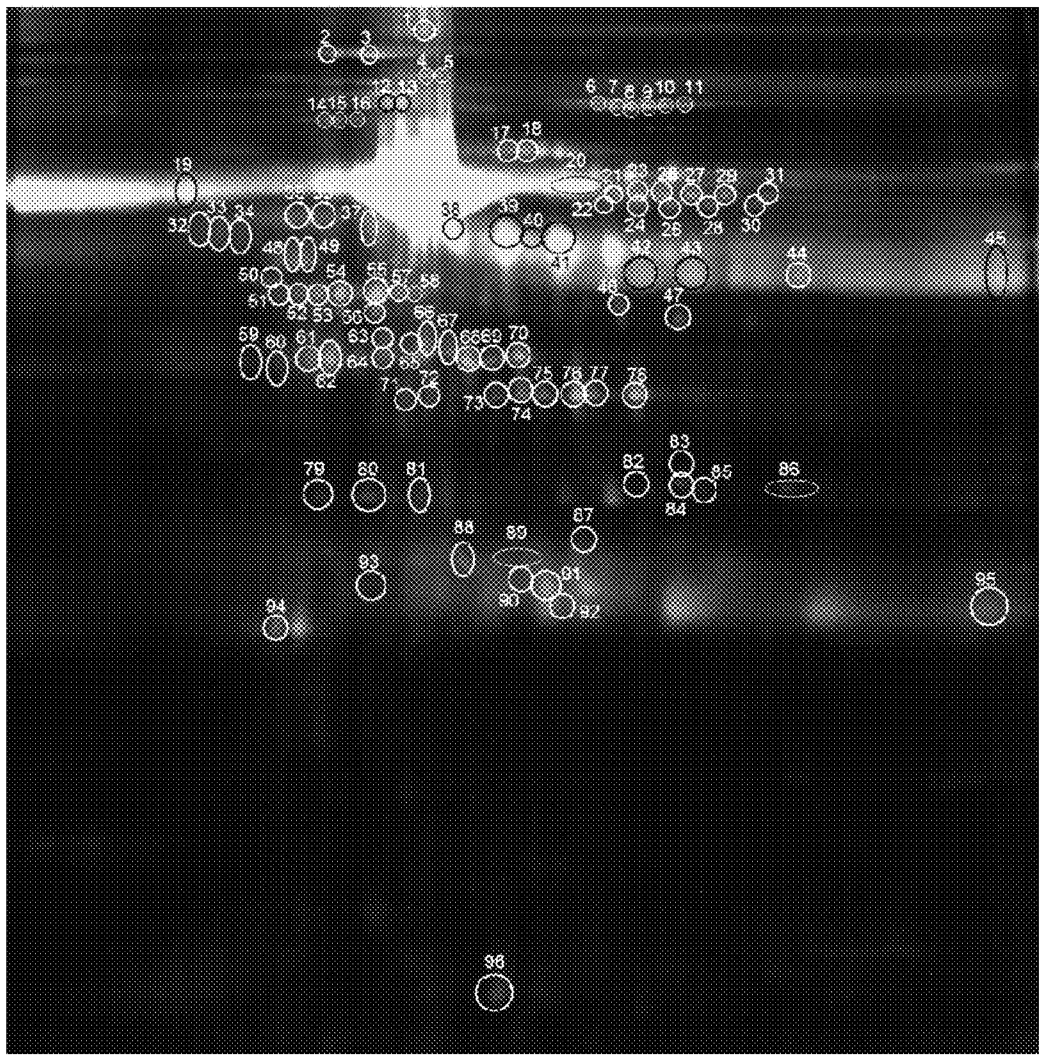
FIG. 1D is an image showing the overlay of the 2DIGE results in benign (green in original) and stage I (red in original) lung samples.
Figure 1E:
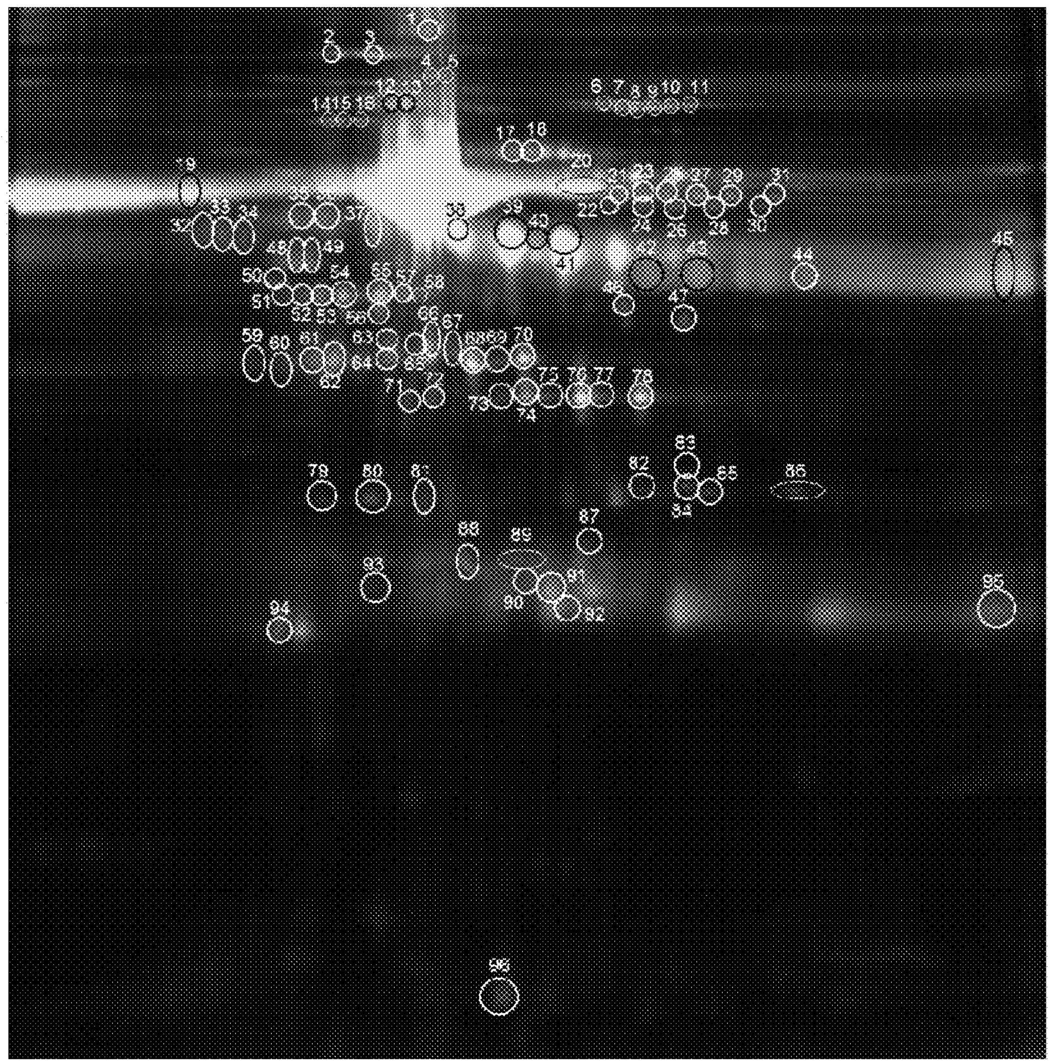
FIG. 1E is an image showing the overlay of the 2DIGE results in benign (green in original) and stage III (red in original) lung samples.
Figure 1F:
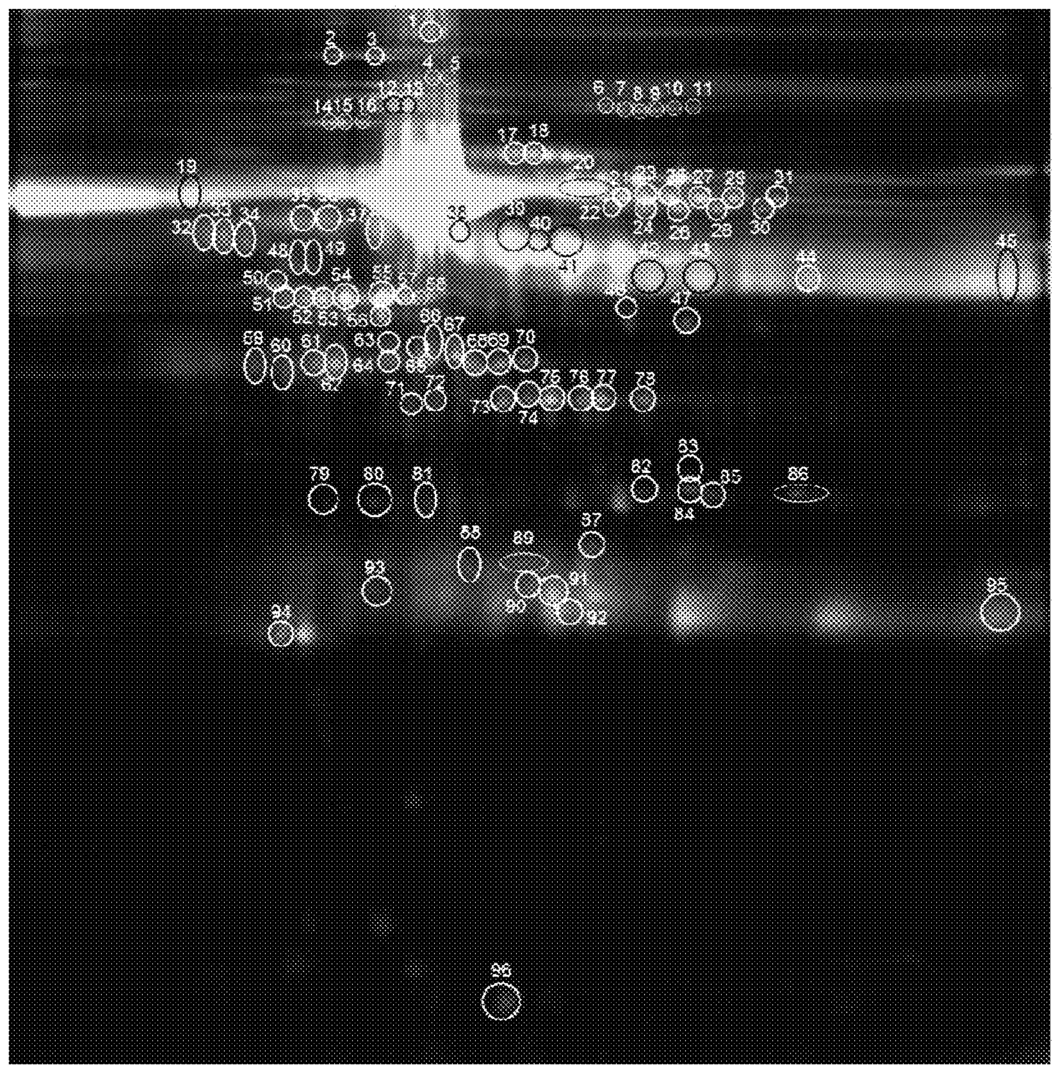
FIG. 1F is an image showing the overlay of the 2DIGE results in stage I (green in original) and stage III (red in original) lung samples.
Figure 2A:
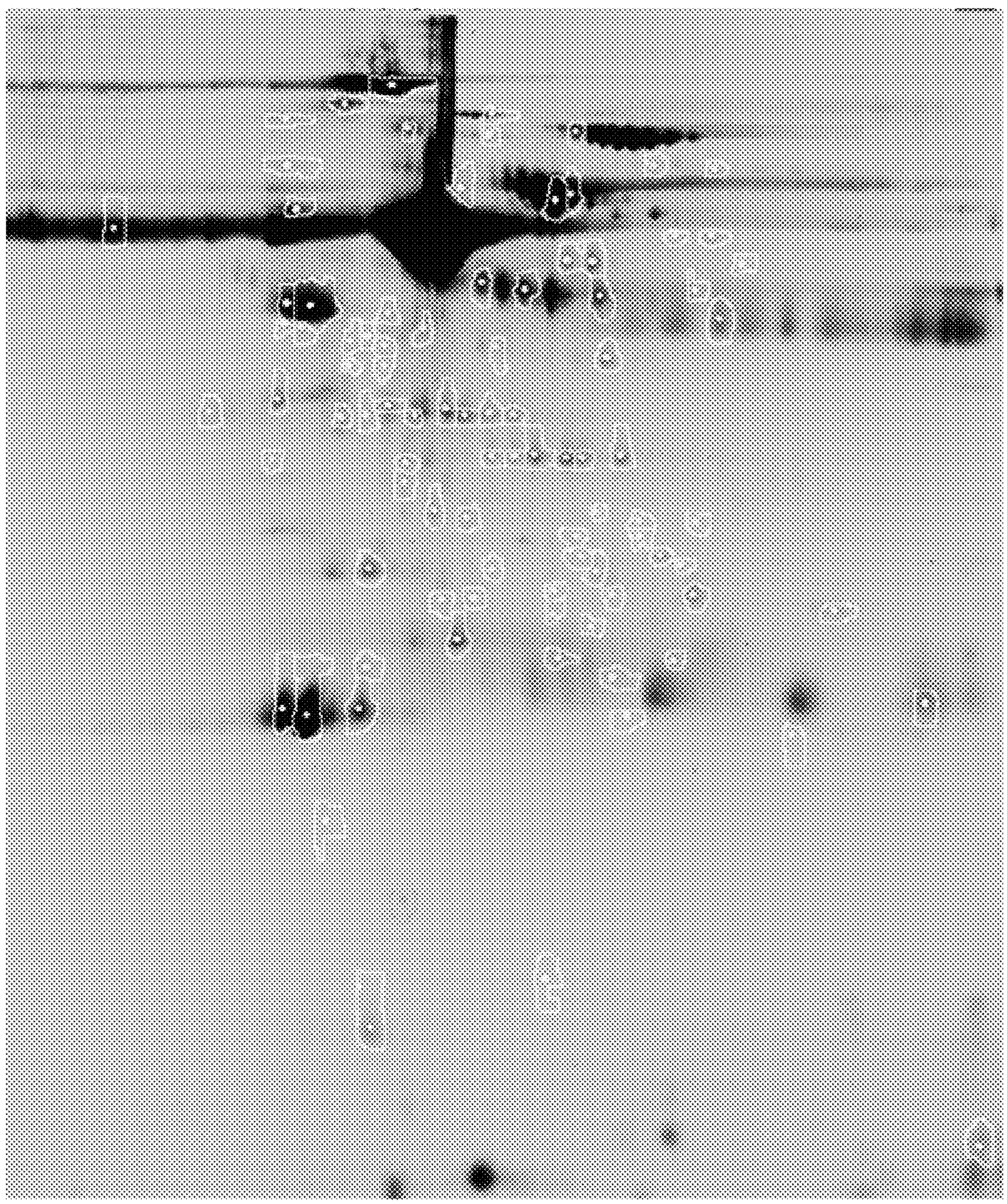
FIGS. 2A-B are images showing the results of 2DIGE analysis of proteins in extracellular vesicle-enriched samples from subjects with benign (2A) and stage I (2B) ovarian disease.
Figure 2B:
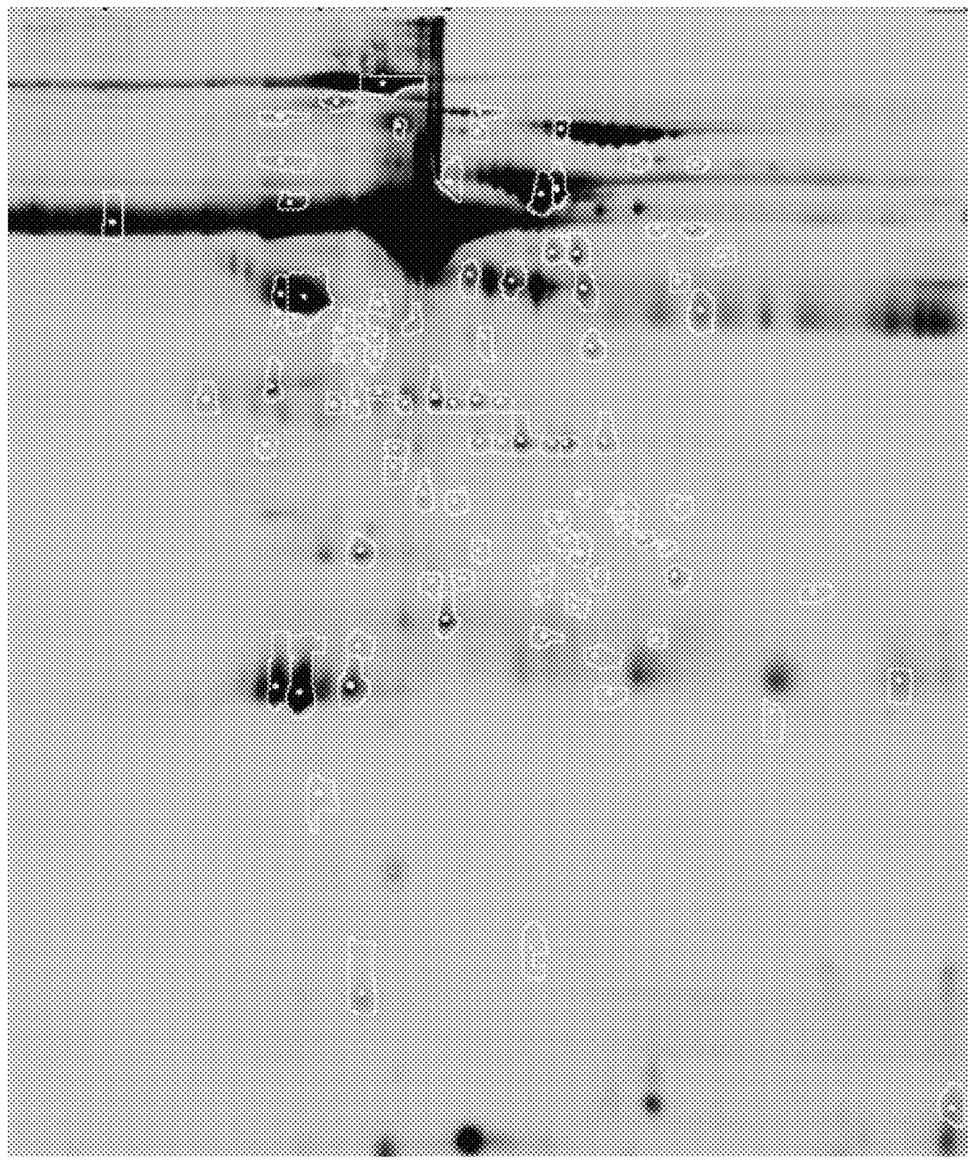
Figure 2C:
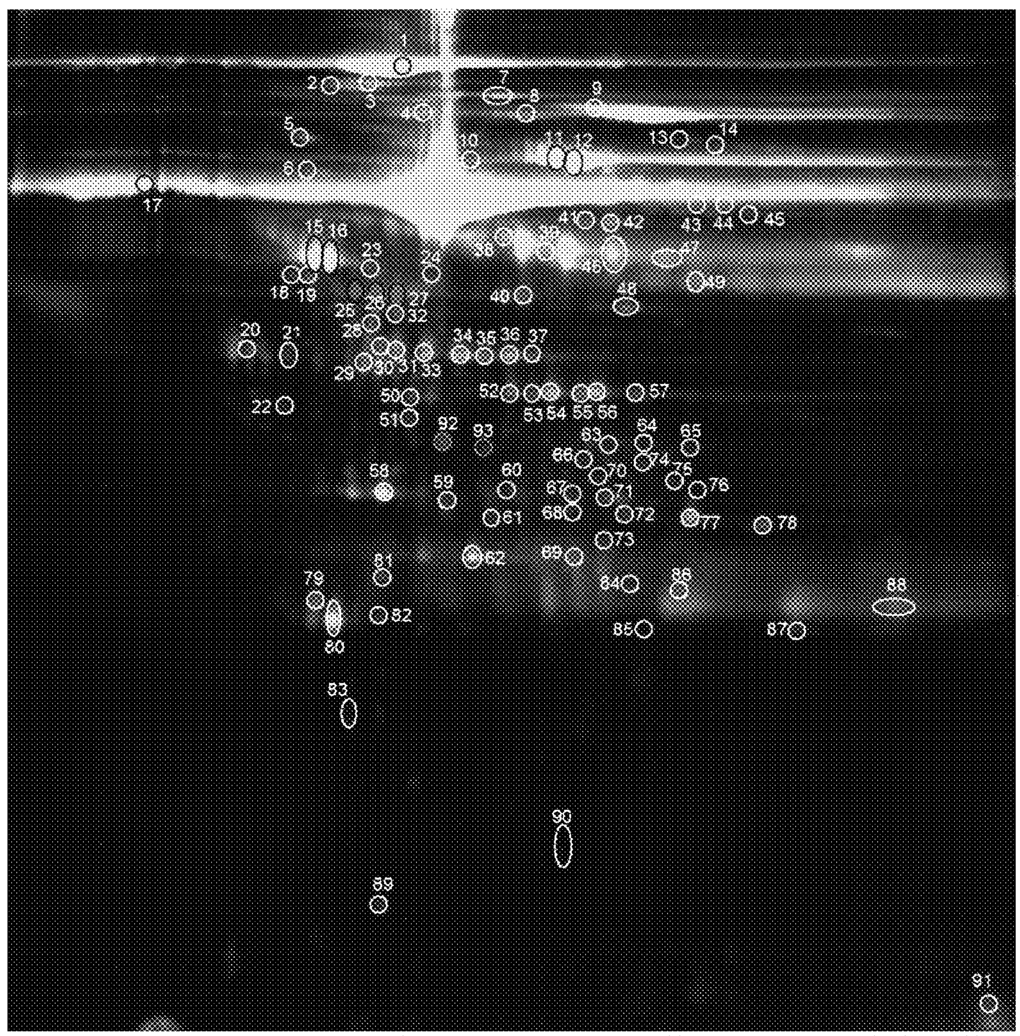
FIG. 2C is an image showing the overlay of the 2DIGE results in benign (green in original) and stage I (red in original) ovarian samples.
Figure 2D:
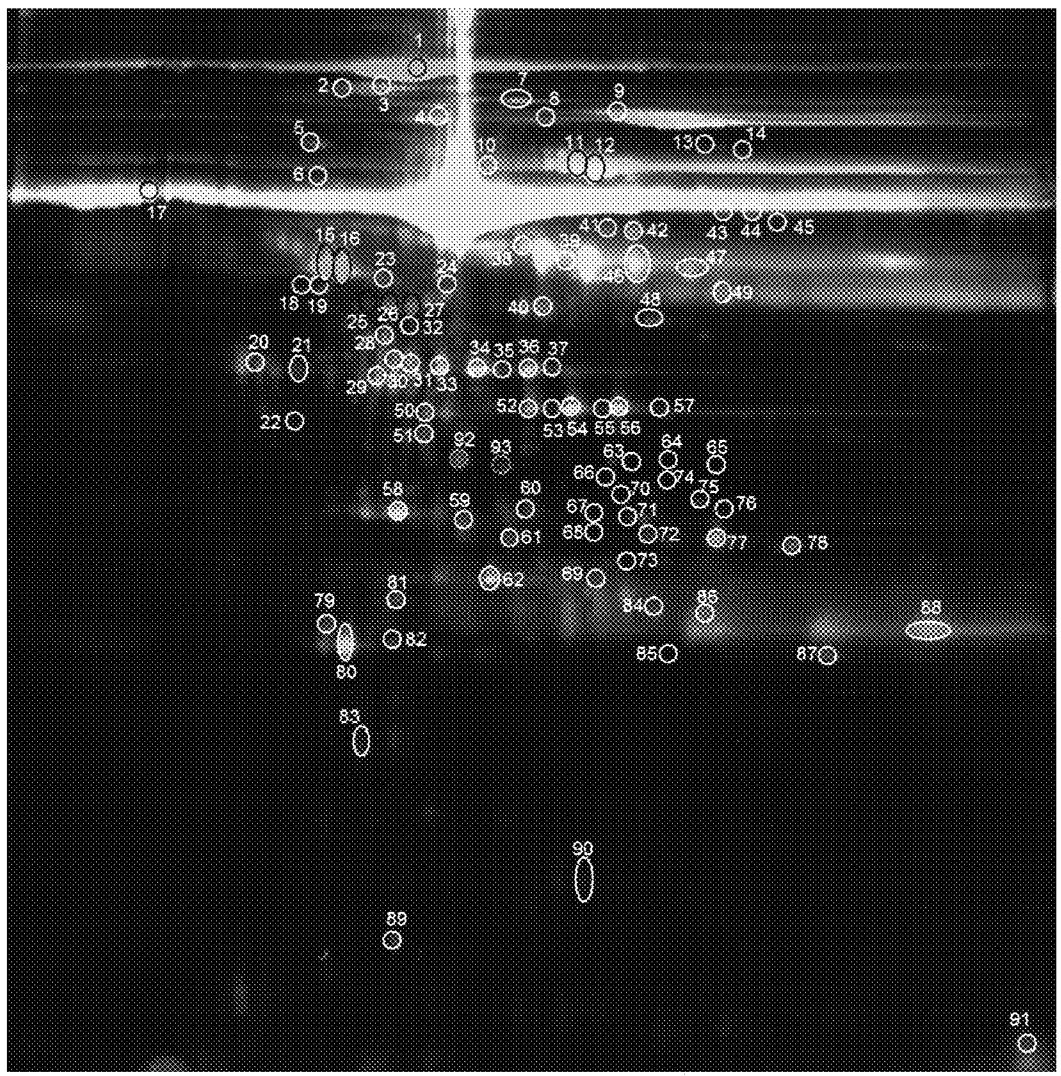
FIG. 2D is an image showing the overlay of the 2DIGE results in benign (green in original) and stage III (red in original) ovarian samples.
Figure 2E:
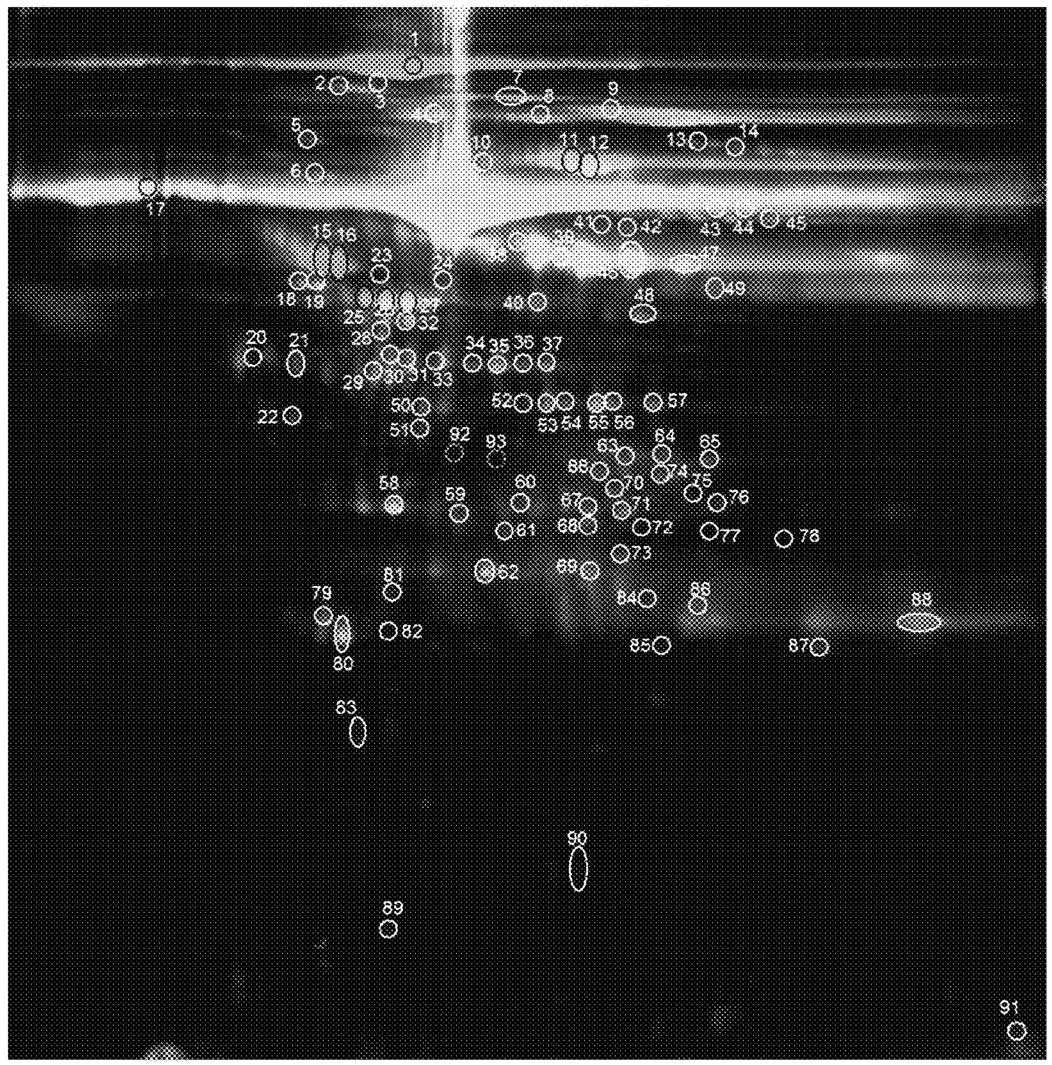
FIG. 2E is an image showing the overlay of the 2DIGE results in stage I (green in original) and stage III (red in original) ovarian samples.

The 2DIGE images were scanned and overlaid, and the differences were quantified. See FIGS. 1A-2E. Statistical analysis and gel-to-gel comparisons were performed with the Biological Variation Analysis module (GE Healthcare).

The 2DIGE profiles demonstrated unique protein distributions correlating with the presence of cancer and early versus late stage disease. The 2DIGE spots were isolated and subjected to identification using tandem mass spectrometry (MS); the results are shown in Table 1 (Lung) and Table 3 (Ovarian). The relative expression levels of some of the proteins were determined in subjects with benign (B), stage I (SI), and stage III (SIM disease; see Tables 2 (Lung) and 4 (Ovarian); proteins for which the identity was determined (as shown in table 1 or 3) are indicated in bold font in tables 2 or 4.

Levels above the baseline level are indicated by a positive ratio; levels below the baseline level are indicated by a negative ratio.

TABLE 1

Lung Cancer

| Spot number | Top Ranked Protein Name (Species) | Accession No. |
|---|---|---|
| 14 | fibrinogen gamma | gi\|223170 |
| 15 | fibrinogen gamma chain, isoform CRA_j [*Homo sapiens*] | gi\|119625320 |
| 16 | Chain A, Human Serum Albumin In A Complex With Myristic Acid And Tri- Iodobenzoic Acid | gi\|157830361 |
| 22 | fibrinogen alpha chain preproprotein, isoform alpha [*Homo sapiens*] | gi\|13591823 |
| 24 | fibrinogen alpha chain preproprotein, isoform alpha [*Homo sapiens*] | gi\|13591823 |
| 26 | fibrinogen alpha chain preproprotein, isoform alpha [*Homo sapiens*] | gi\|13591823 |
| 32 | Chain A, A 2.1 Angstrom Structure Of An Uncleaved Alpha-1-Antitrypsin Shows Variability Of The Rea | gi\|13787109 |
| 33 | Chain A, Alpha1-Antitrypsin | gi\|157831596 |
| 34 | Chain A, Alpha1-Antitrypsin | gi\|157831596 |
| 35 | Chain A, Crystal Structure Of Human Fcari Bound To Iga1-Fc | gi\|31615935 |
| 36 | Chain A, The Intact And Cleaved Human Antithrombin Iii Complex As A Model For Serpin-Proteinase Int | gi\|999513 |
| 37 | Ig Aalpha1 Bur | gi\|223099 |
| 40 | fibrin beta | gi\|223002 |
| 42 | IGHG2 protein [*Homo sapiens*] | gi\|38382776 |
| 43 | IGHG2 protein [*Homo sapiens*] | gi\|38382776 |
| 46 | complement factor H isoform b precursor [*Homo sapiens*] | gi\|62739188 |
| 48 | vitamin D-binding protein/group specific component [*Homo sapiens*] | gi\|455970 |
| 49 | serum vitamin D-binding protein precursor | gi\|181482 |
| 50 | fibrinogen gamma-prime chain [*Homo sapiens*] | gi\|182440 |
| 51 | fibrinogen gamma chain, isoform CRA_j [*Homo sapiens*] | gi\|119625320 |
| 52 | fibrinogen gamma chain, isoform CRA_j [*Homo sapiens*] | gi\|119625320 |
| 53 | fibrinogen gamma chain, isoform CRA_j [*Homo sapiens*] | gi\|119625320 |
| 59 | haptoglobin precursor | gi\|306882 |
| 60 | albumin, isoform CRA_k [*Homo sapiens*] | gi\|119626074 |
| 65 | complement factor H-related 1 [*Homo sapiens*] | gi\|118442839 |
| 67 | complement factor H-related 1 [*Homo sapiens*] | gi\|118442839 |
| 70 | factor H homologue | gi\|183763 |
| 73 | complement factor H-related 1 [*Homo sapiens*] | gi\|118442839 |
| 74 | complement factor H-related 1 [*Homo sapiens*] | gi\|118442839 |
| 75 | complement factor H-related 1 [*Homo sapiens*] | gi\|118442839 |

TABLE 1-continued

| Lung Cancer | | |
|---|---|---|
| Spot number | Top Ranked Protein Name (Species) | Accession No. |
| 77 | complement factor H-related 1 [*Homo sapiens*] | gi\|118442839 |
| 82 | insulin-like growth factor binding protein 2, 36 kDa [*Homo sapiens*] | gi\|55925576 |
| 83 | C2 protein [*Homo sapiens*] | gi\|20987588 |
| 84 | C2 protein [*Homo sapiens*] | gi\|20987588 |
| 85 | insulin-like growth factor binding protein 2, 36 kDa [*Homo sapiens*] | gi\|55925576 |
| 87 | Chain B, Crig Bound To C3c | gi\|119390093 |
| 88 | H factor (complement)-like 3 [*Homo sapiens*] | gi\|5031695 |
| 89 | Ig L-chain V-region [*Homo sapiens*] | gi\|27552515 |
| 90 | albumin, isoform CRA_h [*Homo sapiens*] | gi\|119626071 |
| 92 | Chain A, Crystal Structure Of The Ga Module Complexed With Human Serum Albumin | gi\|55669910 |

TABLE 2

| Lung Ratios | | | |
|---|---|---|---|
| Spot No. | Ratio: S1/B | Ratio: S3/B | Ratio: S3/S1 |
| 1 | −1.79 | −2.82 | −1.69 |
| 2 | −1.74 | −2.21 | −1.37 |
| 3 | −2.70 | −3.21 | −1.27 |
| 4 | −1.78 | −2.05 | −1.23 |
| 5 | −1.94 | −1.98 | −1.09 |
| 6 | −2.08 | −3.25 | −1.67 |
| 7 | −2.61 | −3.48 | −1.43 |
| 8 | −3.17 | −3.71 | −1.25 |
| 9 | −3.80 | −3.87 | −1.09 |
| 10 | −4.07 | −3.77 | 1.01 |
| 11 | −4.25 | −4.09 | −1.03 |
| 12 | −1.99 | −1.18 | 1.58 |
| 13 | −2.07 | −1.22 | 1.59 |
| **14** | **2.70** | **3.83** | **1.33** |
| **15** | **2.32** | **4.08** | **1.65** |
| **16** | **1.58** | **2.88** | **1.71** |
| 17 | 1.88 | 2.94 | 1.46 |
| 18 | 1.26 | 1.61 | 1.19 |
| 19 | −1.81 | −1.65 | 1.02 |
| 20 | −1.82 | −1.64 | 1.03 |
| 21 | 1.61 | 1.59 | −1.09 |
| **22** | **4.49** | **3.43** | **−1.40** |
| 23 | 2.21 | 2.31 | −1.03 |
| **24** | **4.16** | **3.86** | **−1.15** |
| 25 | 1.80 | 1.81 | −1.06 |
| **26** | **3.34** | **3.64** | **1.02** |
| 27 | 2.32 | 2.79 | 1.12 |
| 28 | 2.90 | 3.83 | 1.23 |
| 29 | 2.25 | 2.76 | 1.14 |
| 30 | 2.65 | 3.79 | 1.34 |
| 31 | 2.34 | 3.18 | 1.27 |
| **32** | **4.37** | **11.98** | **2.56** |
| **33** | **2.71** | **5.04** | **1.74** |
| **34** | **1.95** | **3.96** | **1.89** |
| **35** | **1.64** | **2.13** | **1.21** |
| **36** | **−1.08** | **5.12** | **5.16** |
| **37** | **−1.47** | **1.93** | **2.66** |
| 38 | −2.61 | 2.08 | 5.07 |
| 39 | −2.65 | 1.14 | 2.83 |
| **40** | **1.86** | **1.04** | **−1.91** |
| 41 | −2.00 | 1.09 | 2.02 |
| **42** | **2.04** | **−1.08** | **−2.35** |
| **43** | **1.87** | **1.07** | **−1.88** |
| 44 | 1.67 | 1.27 | −1.42 |
| 45 | 1.10 | 2.06 | 1.75 |
| **46** | **−3.27** | **−2.86** | **1.07** |
| 47 | −1.53 | −1.03 | 1.39 |
| **48** | **−6.63** | **−4.29** | **1.44** |
| **49** | **−8.85** | **−5.35** | **1.55** |
| **50** | **4.04** | **4.35** | **1.00** |

TABLE 2-continued

| Lung Ratios | | | |
|---|---|---|---|
| Spot No. | Ratio: S1/B | Ratio: S3/B | Ratio: S3/S1 |
| **51** | **4.67** | **3.10** | **−1.62** |
| **52** | **4.94** | **2.84** | **−1.87** |
| **53** | **3.28** | **2.00** | **−1.75** |
| 54 | 2.60 | 2.36 | −1.18 |
| 55 | 2.33 | 2.76 | 1.10 |
| 56 | 2.41 | 2.27 | −1.14 |
| 57 | 1.49 | 1.69 | 1.06 |
| 58 | 1.73 | 1.99 | 1.08 |
| **59** | **2.21** | **4.87** | **2.06** |
| **60** | **1.35** | **2.13** | **1.47** |
| 61 | −1.74 | −1.45 | 1.12 |
| 62 | −1.81 | −1.44 | 1.17 |
| 63 | −2.74 | 1.09 | 2.79 |
| 64 | −1.97 | 1.01 | 1.85 |
| **65** | **2.31** | **1.87** | **−1.33** |
| 66 | −6.12 | −1.08 | 5.31 |
| **67** | **3.03** | **2.27** | **−1.43** |
| 68 | −13.19 | −1.03 | 11.96 |
| 69 | 1.79 | 1.53 | −1.25 |
| **70** | **−37.00** | **−1.71** | **20.17** |
| 71 | −2.12 | −1.67 | 1.19 |
| 72 | −2.02 | −1.49 | 1.27 |
| **73** | **3.45** | **3.47** | **−1.06** |
| **74** | **−11.41** | **1.37** | **14.64** |
| **75** | **6.07** | **4.70** | **−1.39** |
| 76 | −25.29 | 1.09 | 25.81 |
| **77** | **1.57** | **1.60** | **−1.05** |
| 78 | −30.63 | −1.55 | 18.39 |
| 79 | −6.44 | −2.81 | 2.14 |
| 80 | −6.09 | −2.48 | 2.29 |
| 81 | −2.22 | −1.81 | 1.15 |
| **82** | **−1.26** | **3.11** | **3.66** |
| **83** | **−1.03** | **2.33** | **2.25** |
| **84** | **1.00** | **2.13** | **1.99** |
| **85** | **−1.12** | **3.81** | **3.99** |
| 86 | 1.08 | 2.27 | 1.95 |
| **87** | **1.37** | **1.91** | **1.31** |
| **88** | **−2.09** | **−1.74** | **1.12** |
| **89** | **−1.12** | **1.79** | **1.87** |
| **90** | **1.22** | **2.94** | **2.25** |
| 91 | −1.36 | 1.24 | 1.58 |
| **92** | **1.04** | **2.78** | **2.50** |
| 93 | 1.67 | 2.09 | 1.17 |
| 94 | 1.63 | 1.15 | −1.52 |
| 95 | −1.04 | 1.53 | 1.49 |
| 96 | −1.85 | −1.07 | 1.62 |

TABLE 3

| Ovarian Cancer | | |
|---|---|---|
| Spot number | Top Ranked Protein Name (Species) | Accession No. |
| 3 | complement factor H [*Homo sapiens*] | gi\|177744385 |
| 4 | Chain A, Structure Of Human Serum Albumin With S-Naproxen And The Ga Module | gi\|168988718 |
| 6 | alpha-1-B-glycoprotein - human | gi\|69990 |
| 9 | plasminogen | gi\|190026 |
| 10 | IGHM protein [*Homo sapiens*] | gi\|18044959 |
| 13 | hepatocyte growth factor-like protein | gi\|183977 |
| 14 | hepatocyte growth factor-like protein | gi\|183977 |
| 17 | Chain A, Structure Of Human Serum Albumin With S-Naproxen And The Ga Module | gi\|168988718 |
| 18 | fibrinogen gamma-prime chain [*Homo sapiens*] | gi\|182440 |
| 19 | fibrinogen, gamma chain isoform gamma-B precursor [*Homo sapiens*] | gi\|70906439 |
| 21 | haptoglobin precursor | gi\|306882 |
| 22 | unnamed protein product [*Homo sapiens*] | gi\|110437223 |
| 25 | fibrinogen gamma | gi\|223170 |
| 26 | fibrinogen gamma chain, isoform CRA_o [*Homo sapiens*] | gi\|119625326 |
| 27 | fibrinogen gamma | gi\|223170 |
| 28 | Chain A, Human Serum Albumin In A Complex With Myristic Acid And Tri- Iodobenzoic Acid | gi\|157830361 |
| 29 | Chain A, Structure Of Human Serum Albumin With S-Naproxen And The Ga Module | gi\|168988718 |
| 32 | fibrinogen, gamma chain isoform gamma-A precursor [*Homo sapiens*] | gi\|70906437 |
| 33 | albumin, isoform CRA_k [*Homo sapiens*] | gi\|119626074 |
| 40 | Chain A, Structure Of Human Serum Albumin With S-Naproxen And The Ga Module | gi\|168988718 |
| 45 | fibrinogen, alpha polypeptide isoform alpha pre-proprotein [*Homo sapiens*] | gi\|11761629 |
| 46 | fibrinogen beta chain, isoform CRA_d [*Homo sapiens*] | gi\|119625338 |
| 47 | fibrin beta | gi\|223002 |
| 49 | hypothetical protein [*Homo sapiens*] | gi\|34365137 |
| 50 | PRO2675 [*Homo sapiens*] | gi\|7770217 |
| 52 | complement factor H-related 1 [*Homo sapiens*] | gi\|118442839 |
| 53 | factor H homologue | gi\|183763 |
| 55 | factor H homologue | gi\|183763 |
| 59 | Chain A, Crystal Structure Of The Ga Module Complexed With Human Serum Albumin | gi\|55669910 |
| 63 | fibrinogen A alpha-chain [human, kidney, Peptide Partial Mutant, 200 aa] | gi\|300313 |
| 67 | fibrinogen A alpha-chain [human, kidney, Peptide Partial Mutant, 200 aa] | gi\|300313 |
| 76 | insulin-like growth factor binding protein 2, 36 kDa [*Homo sapiens*] | gi\|55925576 |
| 77 | migration stimulation factor FN70 [*Homo sapiens*] | gi\|12053817 |
| 78 | migration stimulation factor FN70 [*Homo sapiens*] | gi\|12053817 |
| 92 | Chain A, Solution Structure Of The N-Terminal Scr-15 fragment of Complement Factor H | gi\|158430178 |
| 94 | Kallikrein B, plasma (Fletcher factor) 1 [*Homo sapiens*] | gi\|109659056 |
| 95 | kallikrein B, plasma (Fletcher factor) 1, isoform CRA_a [*Homo sapiens*] | gi\|119625027 |
| 96 | kallikrein B, plasma (Fletcher factor) 1, isoform CRA_a [*Homo sapiens*] | gi\|119625027 |
| 99 | Chain A, Alpha1-Antitrypsin | gi\|157831596 |
| 100 | Chain A, Alpha1-Antitrypsin | gi\|157831596 |
| 101 | HP protein [*Homo sapiens*] | gi\|47124562 |
| 102 | haptoglobin [*Homo sapiens*] | gi\|1212947 |
| 103 | albumin, isoform CRA_h [*Homo sapiens*] | gi\|119626071 |
| 105 | haptoglobin Hp2 | gi\|223976 |

TABLE 4

| Ovarian Ratios | | | |
|---|---|---|---|
| Protein ID | SI/B | SIII/B | SIII/SI |
| 1 | −1.07 | −63.29 | −48.19 |
| 2 | 1.58 | −1.70 | −2.17 |
| **3** | **−4.96** | **−21.95** | **−3.59** |
| **4** | **1.15** | **2.42** | **2.59** |
| 5 | 1.07 | −12.80 | −11.15 |

TABLE 4-continued

| Ovarian Ratios | | | |
|---|---|---|---|
| Protein ID | SI/B | SIII/B | SIII/SI |
| **6** | **2.41** | **−1.85** | **−3.63** |
| 7 | 2.19 | −11.45 | −20.30 |
| 8 | 4.83 | −3.45 | −13.54 |
| **9** | **1.93** | **−11.65** | **−18.29** |
| **10** | **−1.34** | **6.05** | **10.00** |

TABLE 4-continued

| Ovarian Ratios | | | |
|---|---|---|---|
| Protein ID | SI/B | SIII/B | SIII/SI |
| 11 | −1.61 | −5.38 | −2.71 |
| 12 | −2.33 | −4.89 | −1.70 |
| **13** | **4.13** | **2.07** | **−1.61** |
| **14** | **3.04** | **−1.05** | **−2.58** |
| 15 | −1.07 | −21.96 | −16.62 |
| 16 | −1.64 | −36.22 | −17.93 |
| **17** | **−1.43** | **2.37** | **4.19** |
| **18** | **33.92** | **10.85** | **−2.54** |
| **19** | **13.64** | **5.38** | **−2.06** |
| 20 | −8.89 | −7.24 | 1.51 |
| **21** | **1.82** | **1.70** | **1.15** |
| **22** | **4.01** | **−1.72** | **−5.58** |
| 23 | −3.29 | −5.41 | −1.33 |
| 24 | 1.54 | 3.14 | 2.51 |
| **25** | **39.93** | **7.53** | **−4.30** |
| **26** | **35.34** | **9.17** | **−3.13** |
| **27** | **60.74** | **18.64** | **−2.64** |
| **28** | **−1.68** | **2.23** | **4.62** |
| **29** | **−1.78** | **2.45** | **5.38** |
| 30 | −1.54 | 2.03 | 3.83 |
| 31 | −2.10 | −1.43 | 1.81 |
| **32** | **42.60** | **6.90** | **−5.01** |
| **33** | **−2.21** | **−1.83** | **1.49** |
| 34 | −23.66 | −1.73 | 16.82 |
| 35 | 3.73 | −1.75 | −5.29 |
| 36 | −9.72 | −1.73 | 6.93 |
| 37 | 2.69 | −1.46 | −3.20 |
| 38 | −1.64 | 2.89 | 5.87 |
| 39 | 3.65 | 3.13 | 1.06 |
| **40** | **−1.09** | **2.58** | **3.45** |
| 41 | −1.52 | −1.13 | 1.66 |
| 42 | −2.98 | −2.20 | 1.67 |
| 43 | 6.76 | 3.66 | −1.50 |
| 44 | 5.40 | 3.05 | −1.44 |
| **45** | **44.52** | **12.25** | **−2.95** |
| **46** | **2.20** | **4.14** | **2.32** |
| **47** | **5.73** | **5.69** | **1.22** |
| 48 | 1.98 | −2.29 | −3.69 |
| **49** | **−2.16** | **−1.82** | **1.46** |
| **50** | **−1.56** | **2.43** | **4.68** |
| 51 | −2.47 | 2.59 | 7.90 |
| **52** | **−21.01** | **−1.55** | **16.66** |
| **53** | **6.01** | **−1.50** | **−7.33** |
| 54 | −16.42 | −1.73 | 11.69 |
| **55** | **6.47** | **−1.67** | **−8.75** |
| 56 | −4.62 | −1.99 | 2.85 |
| 57 | 2.38 | −1.83 | −3.53 |
| 58 | −1.60 | −2.27 | −1.15 |
| **59** | **−1.61** | **2.27** | **4.50** |
| 60 | 1.19 | 2.10 | 2.17 |
| 61 | −1.22 | 2.69 | 4.05 |
| 62 | −1.35 | −2.06 | −1.24 |
| **63** | **22.72** | **−1.06** | **−19.63** |
| 64 | 28.74 | −1.31 | −30.63 |
| 65 | 21.50 | −1.68 | −29.39 |
| 66 | 4.12 | −1.17 | −3.92 |
| **67** | **7.25** | **−1.88** | **−11.05** |
| 68 | 9.46 | −6.90 | −52.95 |
| 69 | 4.01 | −1.17 | −3.82 |
| 70 | 10.19 | 1.92 | −4.31 |
| 71 | 7.09 | 1.75 | −3.28 |
| 72 | −5.42 | −13.47 | −2.02 |
| 73 | 7.10 | −1.05 | −6.03 |
| 74 | 31.60 | 2.01 | −12.76 |
| 75 | −1.63 | −4.00 | −1.99 |
| **76** | **4.87** | **2.58** | **−1.53** |
| **77** | **−35.80** | **−52.38** | **−1.19** |
| **78** | **−28.88** | **−43.88** | **−1.23** |
| 79 | 1.43 | −11.45 | −13.29 |
| 80 | −2.18 | −3.49 | −1.30 |
| 81 | −2.48 | −3.59 | −1.18 |
| 82 | −5.28 | −4.62 | 1.41 |
| 83 | −1.79 | 2.22 | 4.90 |
| 84 | −2.93 | 2.45 | 8.85 |
| 85 | 3.57 | −1.27 | −3.69 |
| 86 | −1.90 | −1.12 | 2.09 |

TABLE 4-continued

| Ovarian Ratios | | | |
|---|---|---|---|
| Protein ID | SI/B | SIII/B | SIII/SI |
| 87 | −1.39 | 1.65 | 2.84 |
| 88 | −1.75 | 8.12 | 17.54 |
| 89 | −2.46 | −3.79 | −1.25 |
| 90 | −1.98 | 2.26 | 5.52 |
| 91 | −2.97 | −5.34 | −1.46 |
| **92** | **−11.97** | **−4.73** | **3.12** |
| 93 | −7.21 | −68.98 | −7.77 |

Certain proteins were common to both lung and ovarian cancers, i.e., were identified in samples from both lung and ovarian cancers; it is believed that these proteins can be used to detect epithelial cancers in general. These proteins are listed in Table 5.

TABLE 5

| Common Proteins | | |
|---|---|---|
| Protein Name (Species) | Accession No. | Increased or Decreased in Cancer |
| fibrinogen gamma | gi\|223170 | increased |
| fibrinogen gamma chain, isoform CRA_o [*Homo sapiens*] | gi\|119625326 | increased |
| Chain A, Human Serum Albumin In A Complex With Myristic Acid And Tri-Iodobenzoic Acid | gi\|157830361 | increased |
| albumin, isoform CRA_k [*Homo sapiens*] | gi\|119626074 | Increased lung/ decreased ovarian |
| fibrin beta | gi\|223002 | increased |
| complement factor H-related 1 [*Homo sapiens*] | gi\|118442839 | Increased/ decreased |
| factor H homologue | gi\|183763 | Decreased SI? |
| Chain A, Crystal Structure Of The Ga Module Complexed With Human Serum Albumin | gi\|55669910 | mixed |
| insulin-like growth factor binding protein 2, 36 kDa [*Homo sapiens*] | gi\|55925576 | mixed |
| albumin, isoform CRA_h [*Homo sapiens*] | gi\|119626071 | |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for diagnosing lung cancer in a subject, the method comprising:

obtaining a sample from the subject;

enriching the sample for extracellular vesicles;

performing an assay to detect a level of one or more proteins selected from the group consisting of: fibrinogen gamma, isoform CRA_j of fibrinogen gamma, serum albumin, isoform alpha of fibrinogen alpha preproprotein, alpha-1-antitrypsin, Fc region of IgA1, fibrin beta, IGHG2, complement factor H isoform b precursor, serum vitamin D-binding protein precursor, haptoglobin precursor, isoform CRA_k of albumin, complement factor H-related 1, factor H homologue, C2 protein, complement C3 alpha chain, and isoform CRA_h of albumin, in the extracellular vesicle-enriched sample, wherein the assay comprises contacting the sample with antibodies or antigen-binding fragments thereof that bind to the protein(s);

comparing the level(s) of the one or more proteins in the extracellular vesicle-enriched sample to reference level(s) of the one or more proteins; and diagnosing lung cancer in a subject having:

(i) an elevated level, as compared to the reference level, of one or more of proteins selected from the group consisting of fibrinogen gamma, isoform CRA_j of fibrinogen gamma, serum albumin, isoform alpha of fibrinogen alpha preproprotein, alpha-1-antitrypsin, Fc region of IgA1, fibrin beta, IGHG2, haptoglobin precursor, isoform CRA_k of albumin, complement factor H-related 1, C2 protein, complement C3 alpha chain, and isoform CRA_h of albumin; and/or (ii) a decreased level, as compared to the reference level, of one or more proteins selected from group consisting of complement factor H isoform b precursor, serum vitamin D-binding protein precursor, and factor H homologue.

2. A method of diagnosing ovarian cancer in a subject, the method comprising:

obtaining a sample from the subject;

enriching the sample for extracellular vesicles;

performing an assay to detect a level of one or more proteins selected from the group consisting of: complement factor H, serum albumin, hepatocyte growth factor-like protein, fibrinogen gamma, isoform gamma-B of fibrinogen gamma precursor, haptoglobin precursor, isoform CRA_o of fibrinogen gamma, isoform gamma-A of fibrinogen gamma precursor, isoform CRA_k of albumin, isoform alpha of fibrinogen alpha preproprotein, isoform CRA_d of fibrinogen beta, fibrin beta, complement factor H-related 1, insulin-like growth factor binding protein 2, and migration stimulation factor FN70 in the extracellular vesicle-enriched sample, wherein the assay comprises contacting the sample with antibodies or antigen-binding fragments thereof that bind to the protein(s); and comparing the level(s) of the one or more proteins in the extracellular vesicle-enriched sample to reference level(s) of the one or more proteins; and diagnosing ovarian cancer in a subject having:

(i) an elevated level, as compared to the reference level, of one or more of proteins selected from the group consisting of serum albumin, hepatocyte growth factor-like protein, fibrinogen gamma, isoform gamma-B of fibrinogen gamma precursor, haptoglobin precursor, isoform CRA_o of fibrinogen gamma, isoform gamma-A of fibrinogen gamma precursor, isoform alpha of fibrinogen alpha preproprotein, isoform CRA_d of fibrinogen beta, fibrin beta, and insulin-like growth factor binding protein 2;

and/or (ii) a decreased level, as compared to the reference level, of one or more of proteins selected from the group consisting of complement factor H, isoform CRA_k of albumin, complement factor H-related 1, and migration stimulation factor FN70.

3. A method for determining the stage of lung cancer in a subject, the method comprising:

obtaining a sample from the subject;

enriching the sample for extracellular vesicles;

performing an assay to detect a level of one or more proteins selected from the group consisting of antithrombin III, IgA alpha1 Bur, complement factor H-related 1, insulin-like growth factor binding protein 2, C2 protein, and Ig L-chain V-region, in the extracellular vesicle-enriched sample, wherein the assay comprises contacting the sample with antibodies or antigen-binding fragments thereof that bind to the protein; and comparing the level(s) of the one or more proteins in the extracellular vesicle-enriched sample to reference level(s) of the one or more protein; and (i) identifying a subject having an elevated level, as compared to the reference level, of one or more of antithrombin III, IgA alpha1 Bur, complement factor H-related 1, insulin-like growth factor binding protein 2, C2 protein, and Ig L-chain V-region, in the extracellular vesicle-enriched sample as having stage III lung cancer; or (ii) identifying a subject having a decreased level, as compared to the reference level, of one or more of antithrombin III, IgA alpha1 Bur, complement factor H-related 1, insulin-like growth factor binding protein 2, C2 protein, and Ig L-chain V-region, in the extracellular vesicle-enriched sample as having stage I lung cancer.

4. A method for determining the stage of ovarian cancer in a subject, the method comprising:

obtaining a sample from the subject;

enriching the sample for extracellular vesicles;

performing an assay to detect presence or levels of one or more proteins selected from the group consisting of: alpha-1-B-glycoprotein, plasminogen, IGHM protein, serum albumin, PRO2675, factor H homologue, and fibrinogen A alpha chain, in the extracellular vesicle-enriched sample, wherein the assay comprises contacting the sample with antibodies or antigen-binding fragments thereof that bind to the protein; and comparing the level(s) of the proteins in the extracellular vesicle-enriched sample to reference level(s) of the proteins; and (i) identifying a subject having an elevated level, as compared to the reference level, of one or more of alpha-1-B-glycoprotein, plasminogen, factor H homologue, and fibrinogen A alpha-chain, in the extracellular vesicle-enriched sample, and/or having a decreased level, as compared to the reference level, of one or more of IGHM protein, serum albumin, and PRO2675, in the extracellular vesicle-enriched sample, as having stage I ovarian cancer; or (ii) identifying a subject having an elevated level, as compared to the reference level, of one or more of IGHM protein, serum albumin, and PRO2675, in the extracellular vesicle-enriched sample, and/or having a decreased level, as compared to the reference level, of one or more of alpha-1-B-glycoprotein, plasminogen, factor H homologue, and fibrinogen A alpha-chain, in the extracellular vesicle-enriched sample, as having stage III ovarian cancer.

5. The method of claim 1, wherein the subject has a mass that is known or suspected to be cancerous.

6. The method of claim 1, further comprising detecting the presence of a mass in the subject.

7. The method of claim 6, wherein detecting the mass comprises performing one or more imaging studies of the subject.

8. The method of claim 1, further comprising administering a treatment for lung cancer to a subject who has been diagnosed with lung cancer.

9. The method of claim 2, further comprising administering a treatment for ovarian cancer to a subject who has been diagnosed with ovarian cancer.

10. The method of claim 8 wherein the treatment comprises one or more of surgical treatment, chemotherapy, immunotherapy, or radiotherapy.

11. The method of claim 9, wherein the treatment comprises one or more of surgical treatment, chemotherapy, immunotherapy, or radiotherapy.

12. The method of claim 2, wherein the subject has a mass that is known or suspected to be cancerous.

13. The method of claim 2, further comprising detecting the presence of a mass in the subject.

14. The method of claim 13, wherein detecting the mass comprises performing one or more imaging studies of the subject.

15. The method of claim 1, wherein the reference level is a level of the protein in an extracellular vesicle-enriched sample from a subject having benign lung cancer.

16. The method of claim 2, wherein the reference level is a level of the protein in an extracellular vesicle-enriched sample from a subject having benign ovarian cancer.

17. The method of claim 3, wherein the reference level is a level of the protein in an extracellular vesicle-enriched sample from a subject having benign lung cancer.

18. The method of claim 4, wherein the reference level is a level of the protein in an extracellular vesicle-enriched sample from a subject having benign ovarian cancer.

* * * * *